United States Patent
Chang et al.

(10) Patent No.: US 10,122,898 B2
(45) Date of Patent: Nov. 6, 2018

(54) ELECTRONIC DEVICE

(71) Applicant: MediaTek Inc., Hsin-Chu (TW)

(72) Inventors: Yu-Chun Chang, New Taipei (TW); Tsu-Ming Liu, Hsinchu (TW)

(73) Assignee: MEDIATEK INC., Hsin-Chu (TW)

( * ) Notice: Subject to any disclaimer, the term of this patent is extended or adjusted under 35 U.S.C. 154(b) by 78 days.

(21) Appl. No.: 15/003,998

(22) Filed: Jan. 22, 2016

(65) Prior Publication Data

US 2016/0241748 A1    Aug. 18, 2016

Related U.S. Application Data

(60) Provisional application No. 62/116,710, filed on Feb. 16, 2015.

(51) Int. Cl.
| | |
|---|---|
| *H04N 5/225* | (2006.01) |
| *H04N 7/14* | (2006.01) |
| *G06F 3/0488* | (2013.01) |
| *G06K 9/00* | (2006.01) |
| *G06T 3/60* | (2006.01) |
| *H04N 7/15* | (2006.01) |
| *G01N 15/14* | (2006.01) |
| *G01N 21/53* | (2006.01) |
| *G01N 21/55* | (2014.01) |
| *G06F 3/041* | (2006.01) |

(Continued)

(52) U.S. Cl.
CPC ....... *H04N 5/2252* (2013.01); *G01N 15/1434* (2013.01); *G01N 21/53* (2013.01); *G01N 21/55* (2013.01); *G06F 1/1626* (2013.01); *G06F 1/1686* (2013.01); *G06F 3/016* (2013.01); *G06F 3/0414* (2013.01); *G06F 3/0416* (2013.01); *G06F 3/0484* (2013.01); *G06F 3/0488* (2013.01); *G06F 3/16* (2013.01); *G06K 9/00255* (2013.01); *G06T 3/60* (2013.01); *H04M 1/0264* (2013.01); *H04N 5/2253* (2013.01); *H04N 5/2254* (2013.01); *H04N 5/2257* (2013.01); *H04N 7/144* (2013.01); *H04N 7/15* (2013.01); *G01N 2201/062* (2013.01); *G01N 2201/0638* (2013.01); *G06F 2203/04806* (2013.01); *G06F 2203/04808* (2013.01); *H04N 2007/145* (2013.01)

(58) Field of Classification Search
CPC .... H04N 5/2252; H04N 5/2254; G03B 17/02; G03B 17/56; G03B 17/565; G03B 17/566; G03B 2217/00; G03B 2217/002
USPC .................................................. 348/373–375
See application file for complete search history.

(56) References Cited

U.S. PATENT DOCUMENTS 6,033,130 A * 3/2000 Muroi .................... G03B 17/04
                                                         396/448
2005/0179813 A1* 8/2005 Fujii .................... H04N 5/2252
                                                         348/375

(Continued)

*Primary Examiner* — Kelly L Jerabek

(74) *Attorney, Agent, or Firm* — McClure, Qualey & Rodack, LLP

(57) ABSTRACT

An electronic device is provided. The electronic device includes a housing; a camera module disposed in the housing and having a lens outstanding from a surface of the housing; and a protection unit connected to the housing, wherein when the camera module is in an off-state, a top surface of the protection unit is higher than a surface of the lens, when the camera module is in an on-state, the top surface of the protection unit is lower than the surface of the lens.

9 Claims, 23 Drawing Sheets

(51) Int. Cl.
*G06F 3/0484* (2013.01)
*G06F 3/16* (2006.01)
*G06F 3/01* (2006.01)
*G06F 1/16* (2006.01)
*H04M 1/02* (2006.01)

(56) References Cited

U.S. PATENT DOCUMENTS

| | | | |
|---|---|---|---|
| 2006/0012887 A1* | 1/2006 | Kano | G02B 7/282 |
| | | | 359/694 |
| 2007/0193901 A1* | 8/2007 | Cohen | B65D 85/38 |
| | | | 206/316.2 |
| 2008/0019000 A1* | 1/2008 | Lee | G02B 13/001 |
| | | | 359/511 |
| 2011/0001872 A1* | 1/2011 | Honsho | G02B 7/102 |
| | | | 348/362 |
| 2011/0157713 A1* | 6/2011 | Heitkamp | G02B 7/02 |
| | | | 359/673 |
| 2014/0152860 A1* | 6/2014 | Yuge | H04N 5/23287 |
| | | | 348/208.11 |
| 2015/0189140 A1* | 7/2015 | Sutton | H04N 5/2257 |
| | | | 348/208.1 |

* cited by examiner

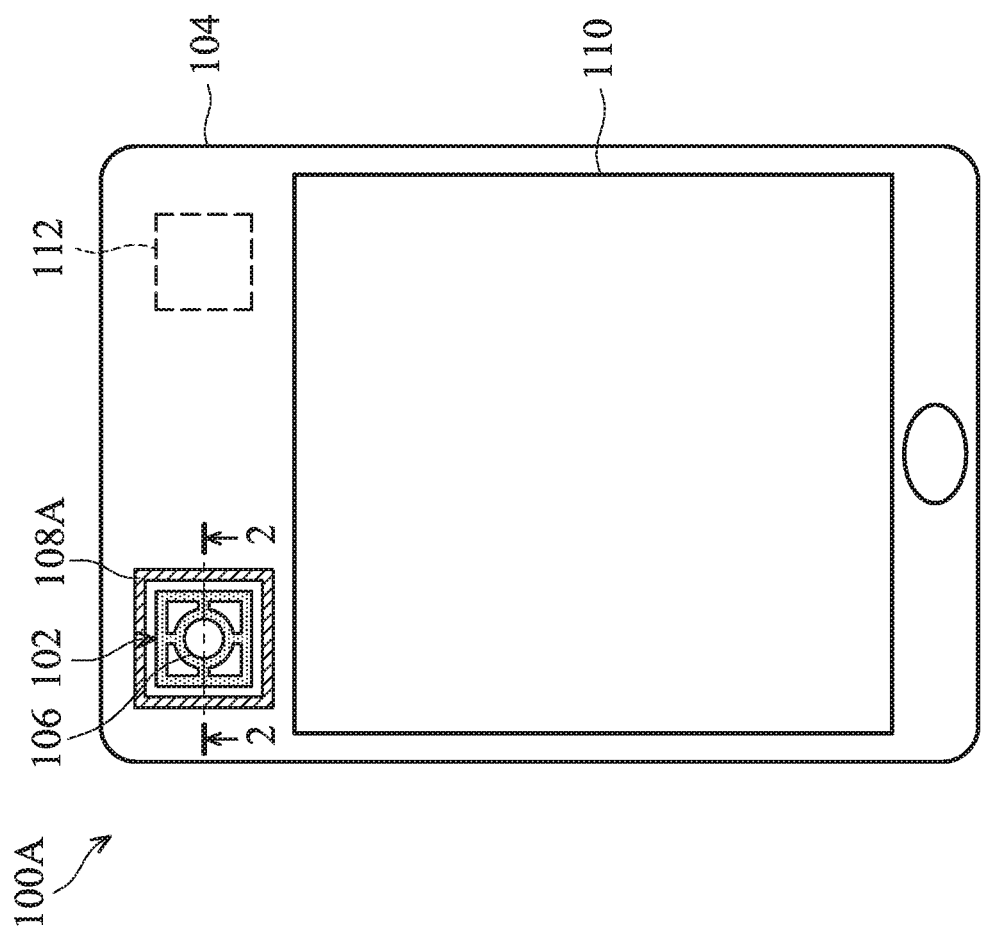

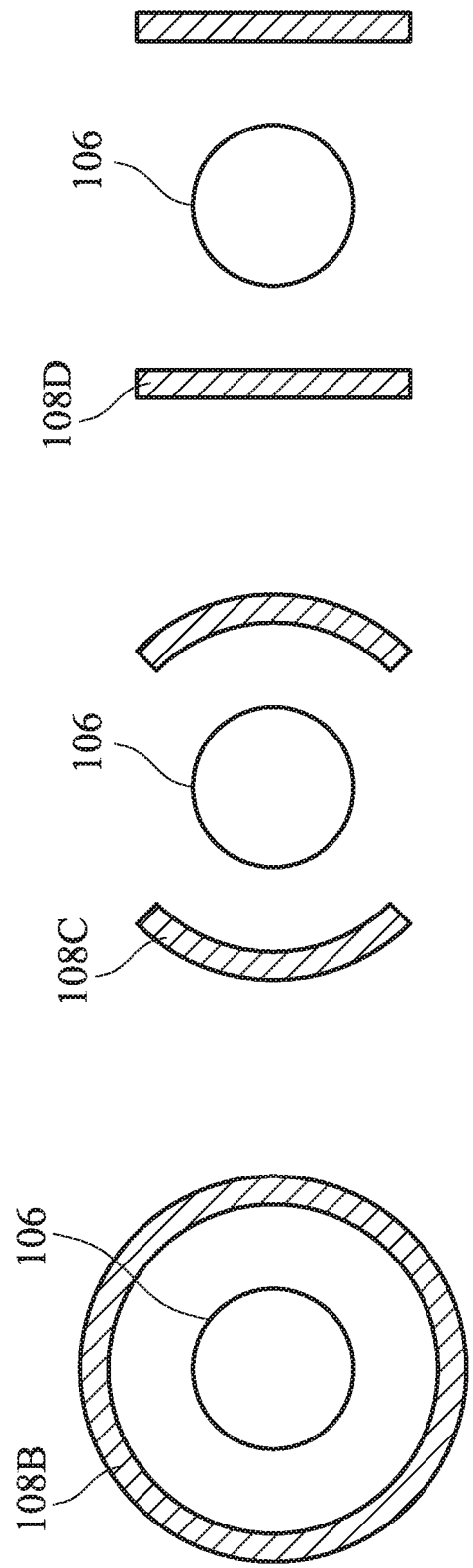

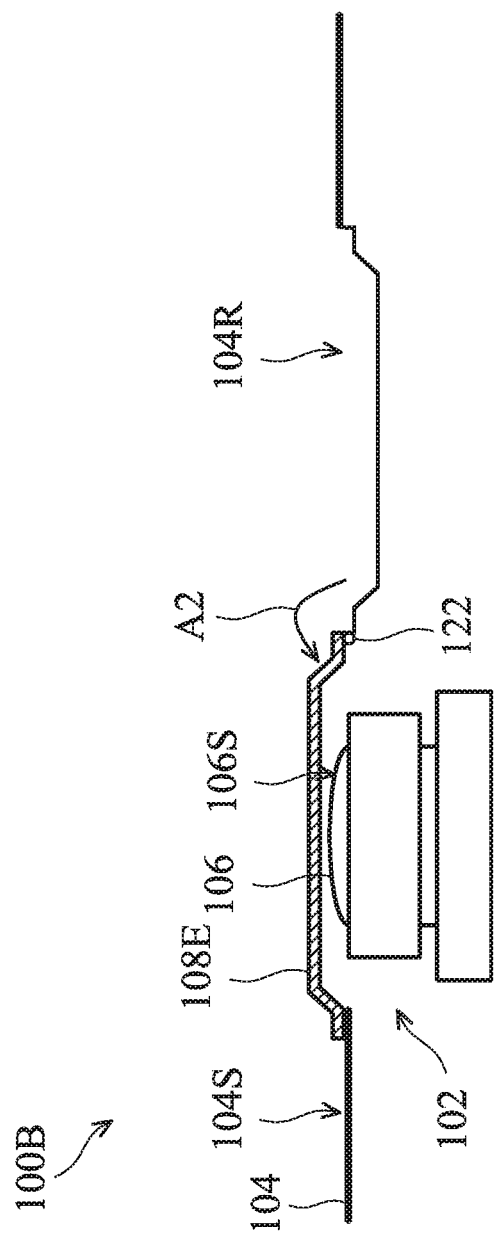

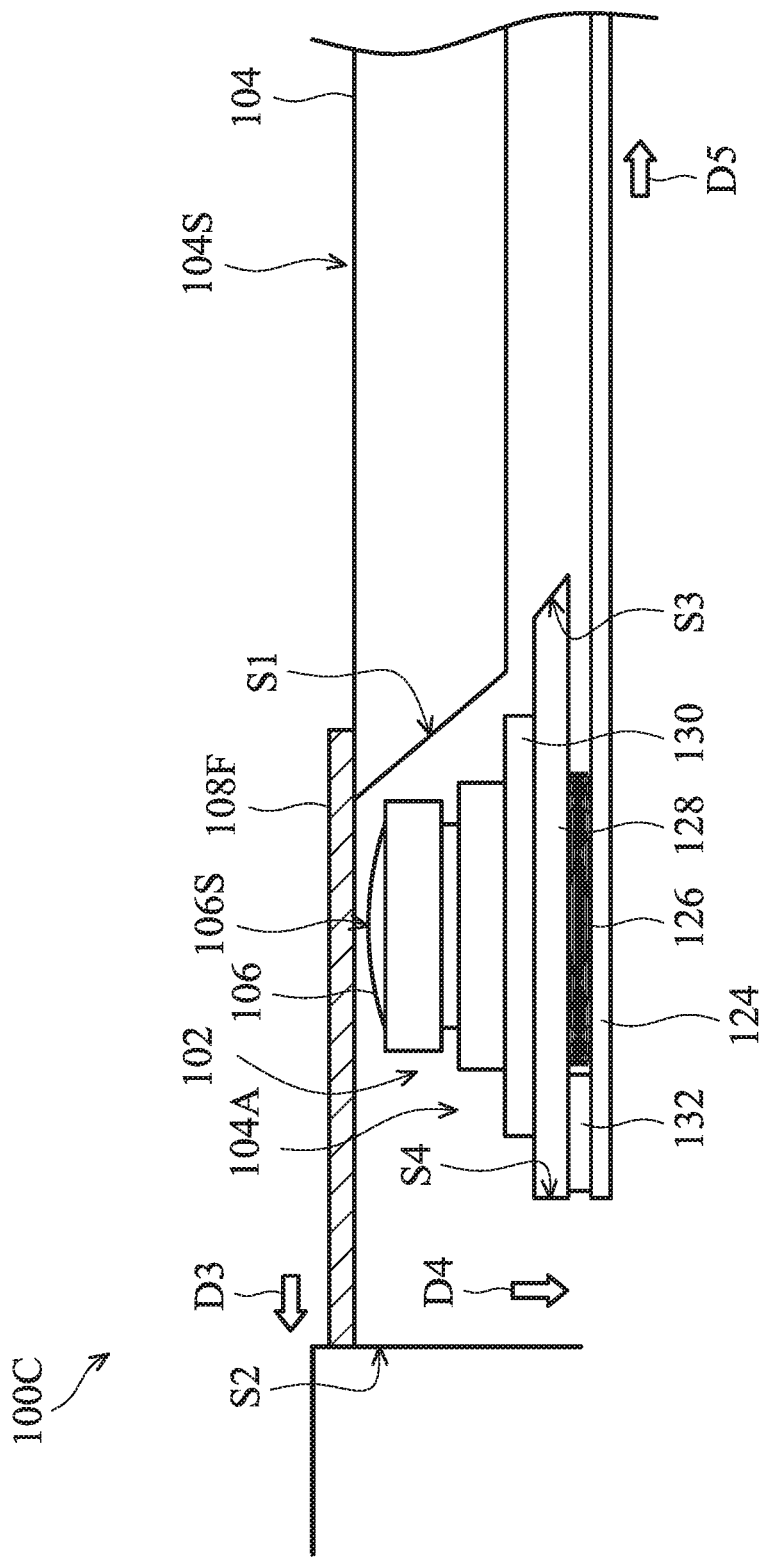

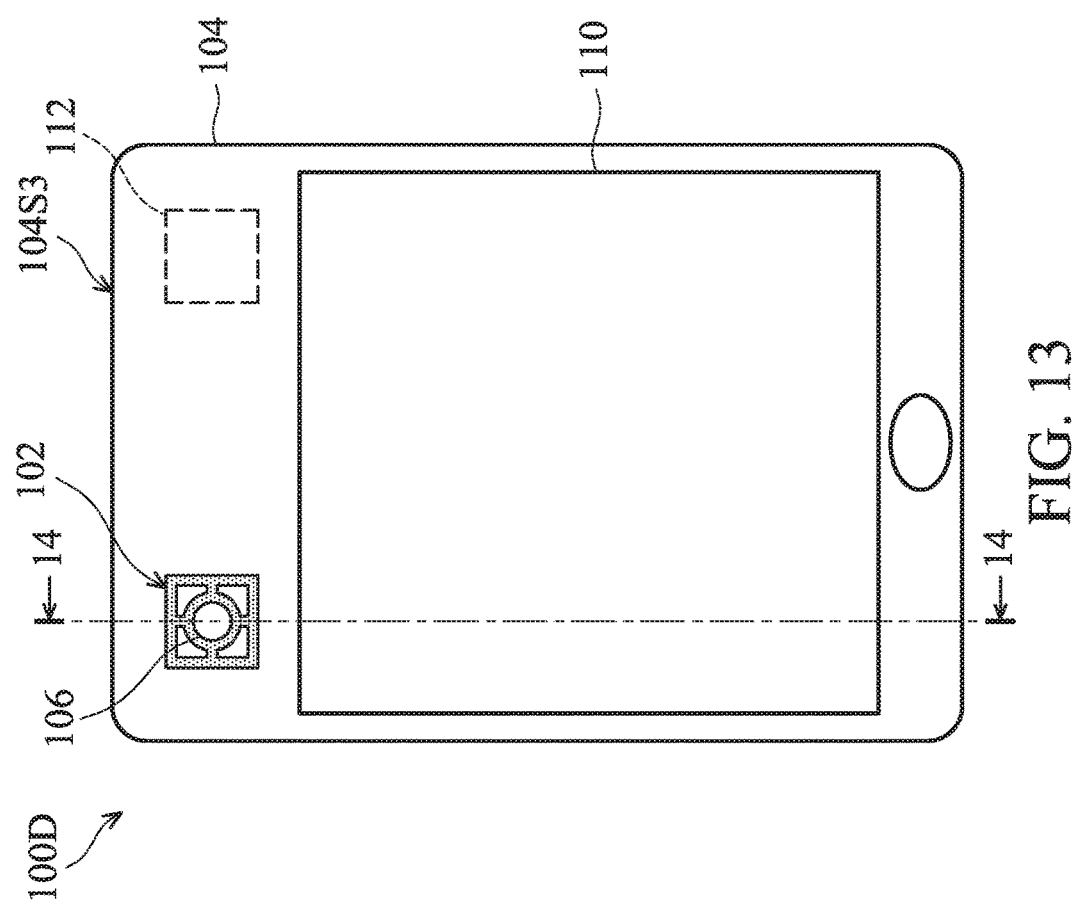

ELECTRONIC DEVICE

CROSS REFERENCE TO RELATED APPLICATIONS

This application claims the benefit of U.S. Provisional Application No. 62/116,710 filed Feb. 16, 2015, and the entirety of which is incorporated by reference herein.

BACKGROUND OF THE INVENTION

Field of the Invention

The disclosure relates to an electronic device, and in particular to an electronic device having a camera module.

Description of the Related Art

In recent years, with the development of photographic and camera technology, a lens with wide field of view, such as a fisheye lens, has become more widely used in electronic devices. However, since the lens has to outstand from the surface of the electronic devices to keep the field of view, the lens can easily become worn down by other objects, such as a table. On the other hand, if an element is designed to be disposed beside the lens or disposed to cover the lens in order to protect the lens from wearing down, the field of view of the lens will be sacrificed due to the element.

Therefore, an electronic device which may prevent the lens from wearing down without losing the field of view is needed.

BRIEF SUMMARY OF THE INVENTION

In some embodiments of the present disclosure, an electronic device is provided. The electronic device includes a housing, a camera module disposed in the housing and having a lens outstanding from a surface of the housing; and a protection unit connected to the housing, wherein when the camera module is in an off-state, a top surface of the protection unit is higher than a surface of the lens, when the camera module is in an on-state, the top surface of the protection unit is lower than the surface of the lens.

In some embodiments of the present disclosure, an electronic device is provided. The electronic device includes a housing; a camera module disposed in the housing and having a lens; and a protection unit connected to the housing, wherein when the camera module is in an off-state, the protection unit covers the lens, when the camera module is in an on-state, the lens outstands from a surface of the housing and the protection unit exposes the lens.

In some embodiments of the present disclosure, an electronic device is provided. The electronic device includes a housing having a first surface and a second surface opposite to each other; and a camera module disposed at an end portion of the housing and having a lens outstanding from the housing, wherein the housing has an arc shape, and the second surface of the housing is a concave surface of the arc shape.

A detailed description is given in the following embodiments with reference to the accompanying drawings.

BRIEF DESCRIPTION OF THE DRAWINGS

The disclosure may be more fully understood by reading the subsequent detailed description and examples with references made to the accompanying drawings, wherein:

FIG. 1 is a top view of an electronic device in accordance with some embodiments of the present disclosure;

FIG. 7A is a schematic diagram illustrating the protection unit and the lens in accordance with some other embodiments of the present disclosure;

FIG. 7B is a schematic diagram illustrating the protection unit and the lens in accordance with some other embodiments of the present disclosure;

FIG. 7C is a schematic diagram illustrating the protection unit and the lens in accordance with some other embodiments of the present disclosure;

FIG. 9A is a cross-sectional view along line 9-9 in FIG. 8A when the camera module is in an off-state in accordance with some embodiments of the present disclosure;

FIG. 11A is a cross-sectional view along line 11-11 in FIG. 10A when the camera module is in an off-state in accordance with some embodiments of the present disclosure;

FIG. 13 is a top view of an electronic device in accordance with some other embodiments of the present disclosure;

DETAILED DESCRIPTION OF THE INVENTION

Figure 2B:
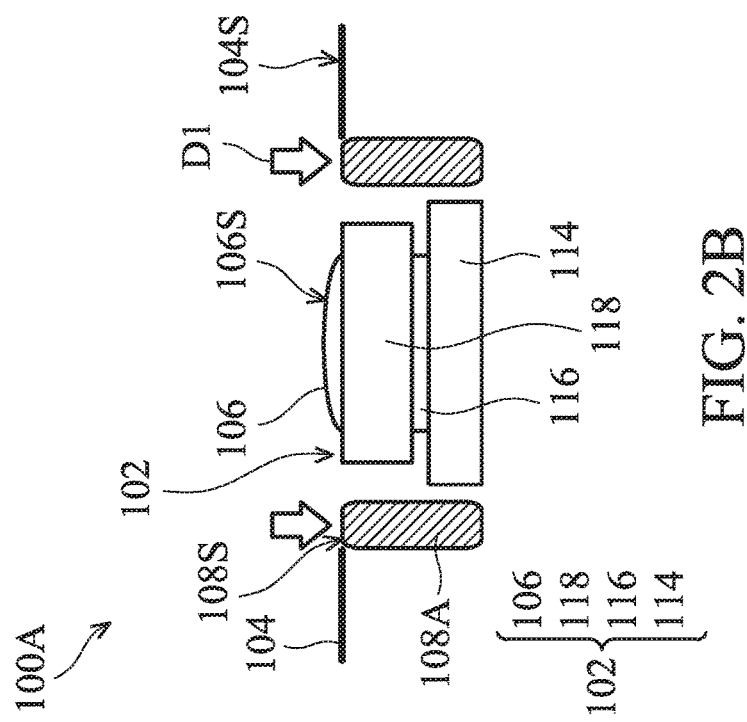
FIG. 2B is a cross-sectional view along line 2-2 in FIG. 1 when the camera module is in an on-state in accordance with some embodiments of the present disclosure.

The electronic device of the present disclosure is described in detail in the following description. In the following detailed description, for purposes of explanation, numerous specific details and embodiments are set forth in order to provide a thorough understanding of the present disclosure. The specific elements and configurations described in the following detailed description are set forth in order to clearly describe the present disclosure. It will be apparent, however, that the exemplary embodiments set forth herein are used merely for the purpose of illustration, and the inventive concept may be embodied in various forms without being limited to those exemplary embodiments. In addition, the drawings of different embodiments may use like and/or corresponding numerals to denote like and/or corresponding elements in order to clearly describe the present disclosure. However, the use of like and/or corresponding numerals in the drawings of different embodiments does not suggest any correlation between different embodiments. This description of the exemplary embodiments is intended to be read in connection with the accompanying drawings, which are to be considered part of the entire written description. The drawings are not drawn to scale. In addition, structures and devices are shown schematically in order to simplify the drawing.

The embodiment of the present disclosure utilizes a movable protection unit which is movable relative to the lens of the camera module in the electronic device or utilizes a housing which has an arc shape to prevent the lens from being worn down without losing the field of view of the lens.

FIG. 1 is a top view of a camera module 102 applied to an electronic device 100A in accordance with some embodiments of the present disclosure. The electronic device 100A may be a hand-held electronic device, such as a mobile phone, tablet, or notebook. Alternatively, the electronic device 100A may be a wearable electronic device, such as a watch. Alternatively, the electronic device 100A may be an automotive electronic device, such as a dash-mounted digital video recorder.

Referring to FIG. 1, the electronic device 100A includes a housing 104 and a camera module 102 disposed in the housing 104. The camera module 102 has a lens 106. The electronic device 100A further includes a protection unit 108A connected to the housing 104 and disposed surrounding or beside the lens 106 or the camera module 102. The material of the protection unit 108A may include metal, plastic, hard plastic, or any other suitable material, or a combination thereof.

In addition, the electronic device 100A further includes a display region 110 and an electrical component 112. The display region 110 can be configured to display information content to be provided by the electronic device 100A and/or any messages or contents that can enable operation, communication, or interaction by the user with the electronic device 100A. Moreover, the display region 110 may be a touch-sensitive display that can not only output information to the user but can also receive input from the user. In addition, the display region can be implanted by a display panel. For example, the display region 110 could include a touch display panel such as a resistive touch panel, a cap touch panel, an optical touch panel or an electromagnetic touch panel.

It should be noted that the exemplary embodiment set forth in FIG. 1 is merely for the purpose of illustration. In some other embodiments of the present disclosure, the electronic device does not include the display region. In some embodiments of the present disclosure, the electronic device may inform the user by a flashlight or any other suitable lighting element disposed on or in the electronic device. Alternatively, in some other embodiments of the present disclosure, the electronic device may inform the user by producing a sound or vibration.

The electrical component 112 may include a processor unit and an application. The application may include a camera application which may use the camera module 102 or any other application that may use the camera module 102. In addition, the electrical component 112 may be disposed in any place of the electronic device 100A to meet design requirements.

It should be understood that unless defined otherwise, all technical and scientific terms used herein have the same meaning as commonly understood by one of ordinary skill in the art to which this disclosure belongs. It should be appreciated that, in each case, the term, which is defined in a commonly used dictionary, should be interpreted as having a meaning that conforms to the relative skills of the present disclosure and the background or the context of the present disclosure, and should not be interpreted in an idealized or overly formal manner unless so defined.

Figure 2A:
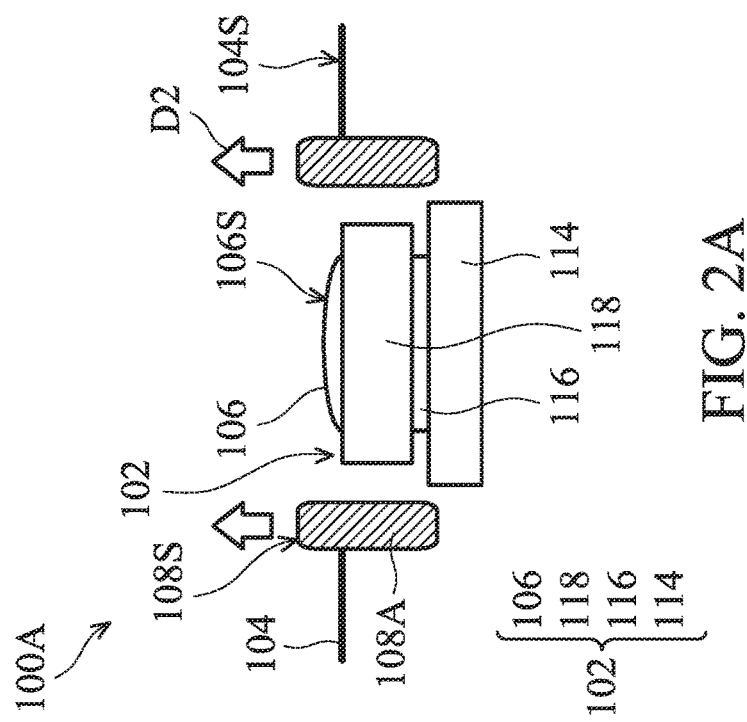
FIG. 2A is a cross-sectional view along line 2-2 in FIG. 1 when the camera module is in an off-state in accordance with some embodiments of the present disclosure.

FIG. 2A is a cross-sectional view along line 2-2 in FIG. 1 when the camera module 102 is in an off-state in accordance with some embodiments of the present disclosure. FIG. 2B is a cross-sectional view along line 2-2 in FIG. 1 when the camera module 102 is in an on-state in accordance with some embodiments of the present disclosure. As shown in FIGS. 2A-2B, the camera module 102 is disposed in the housing 104. In some embodiments of the present disclosure, the camera module 102 may include a substrate 114, a connection portion 116 disposed over the substrate 114, a lens cone 118 connected to the substrate 114 by the connection portion 116, and the lens 106 disposed over the lens cone 118. In addition, the lens 106 outstands or protrudes out from the lens cone 118.

It should be noted that the elements or devices in the drawings of the present disclosure may be present in any form or configuration known to those skilled in the art. In addition, the expression "an element or a unit overlying another element or unit", "an element or a unit is disposed above another element or unit", "an element or a unit is disposed on other element or unit" and "an element or a unit is disposed over other element or unit" may indicate that the element or unit is in direct contact with the other element or unit, or that the element or unit is not in direct contact with the other element or unit, there being one or more intermediate element or units disposed between the element or unit and the other element or unit.

Still referring to FIGS. 2A-2B, the lens 106 outstands from the surface 104S of the housing 104. In some embodiments of the present disclosure, the material of the lens 106 may include glass, plastic, or any other suitable material. In addition, the glass lens is preferred over the plastic lens since glass is harder than plastic and therefore the glass lens is less likely to be worn down compared to the plastic lens.

In addition, in some embodiments of the present disclosure, the lens 106 may be a fisheye lens. The fisheye lens refers to a hemispherical plano-convex lens with a short focal length for photographing in a full field of view of almost or more than 180° in all directions in front of the camera. The focal length of fisheye lens may be between 0.2 mm or 0.4 mm to 20 mm. For example, in some embodiments of the present disclosure, the focal length of fisheye lens may be between 0.2 mm to 2 mm, or between 2 mm to 15 mm, or between 8 mm to 10 mm.

Still referring to FIGS. 2A-2B, the protection unit 108A is movable relative to the lens 106. When the camera module 102 is in the off-state, as shown in FIG. 2A, the top surface 108S of the protection unit 108A is higher than the surface 106S of the lens 106. In addition, when the camera module 102 is in the on-state, as shown in FIG. 2B, the top surface 108S of the protection unit 108A is lower than the surface 106S of the lens 106.

It should be noted that in this specification, relative expressions are used. For example, "lower", "bottom", "higher" or "top" are used to describe the position of one element relative to another. It should be appreciated that if a device is flipped upside down, an element that is "lower" will become an element that is "higher".

Since the protection unit 108A is disposed surrounding or beside the lens 106 and the top surface 108S of the protection unit 108A is higher than the surface 106S of the lens 106 when the camera module 102 is in the off-state, it may prevent the lens from being worn down by other object such as a table. In addition, since the top surface 108S of the protection unit 108A is lower than the surface 106S of the lens 106 when the camera module 102 is in the on-state and is ready to capture photos, the field of view of the lens 106 would not be lost. In other words, the camera module 102 may still be able to capture photos with up to 180° field of view or more. Therefore, by utilizing the movable protection unit 108A which is movable relative to the lens 106 of the camera module 102, the electronic device 100A may prevent the lens 106 from being worn down by other object such as a table without losing the field of view of the lens 106.

Figure 3:
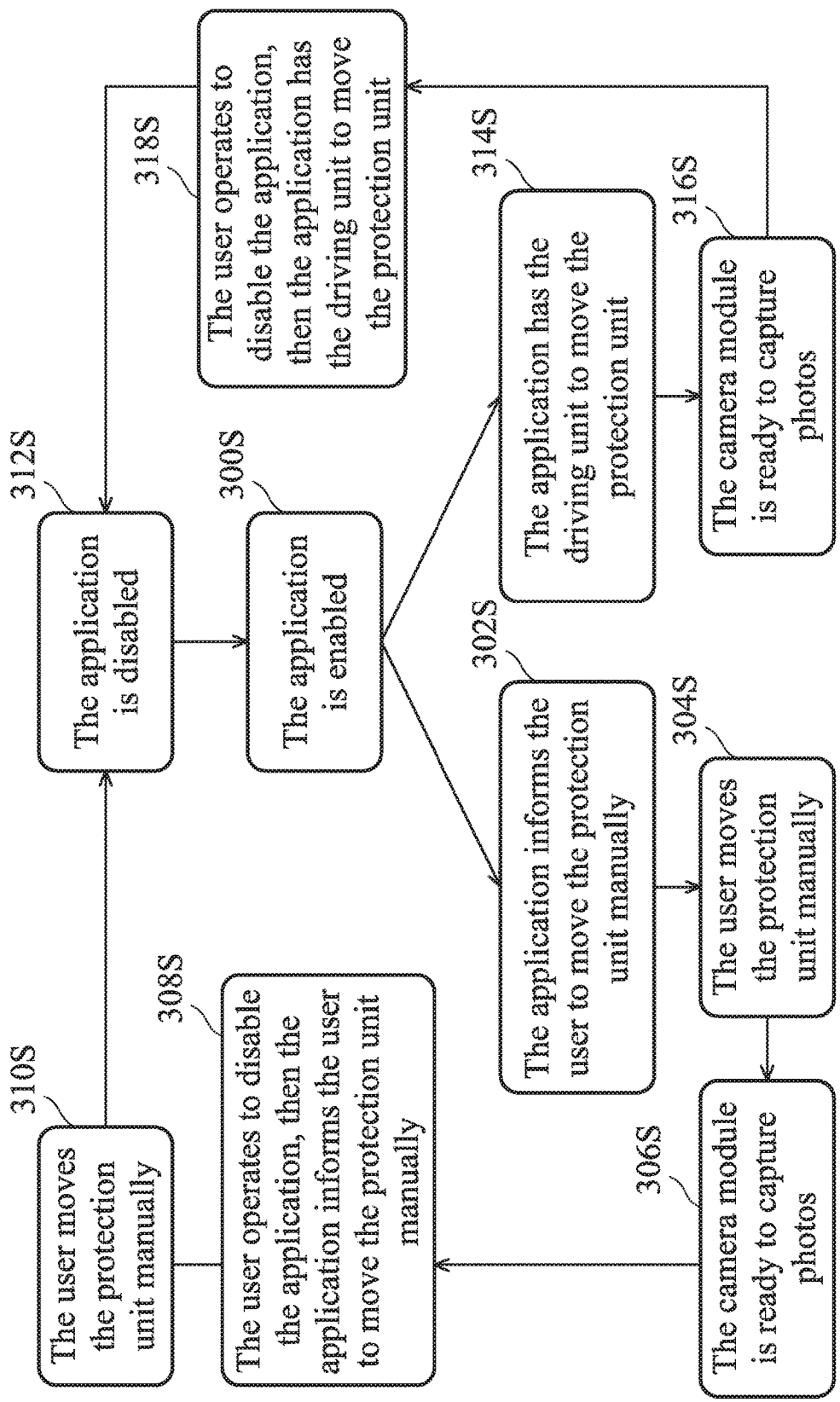
FIG. 3 is a flowchart illustrating an operating method for moving the protection unit according to some embodiments of the present disclosure.
Figure 4:
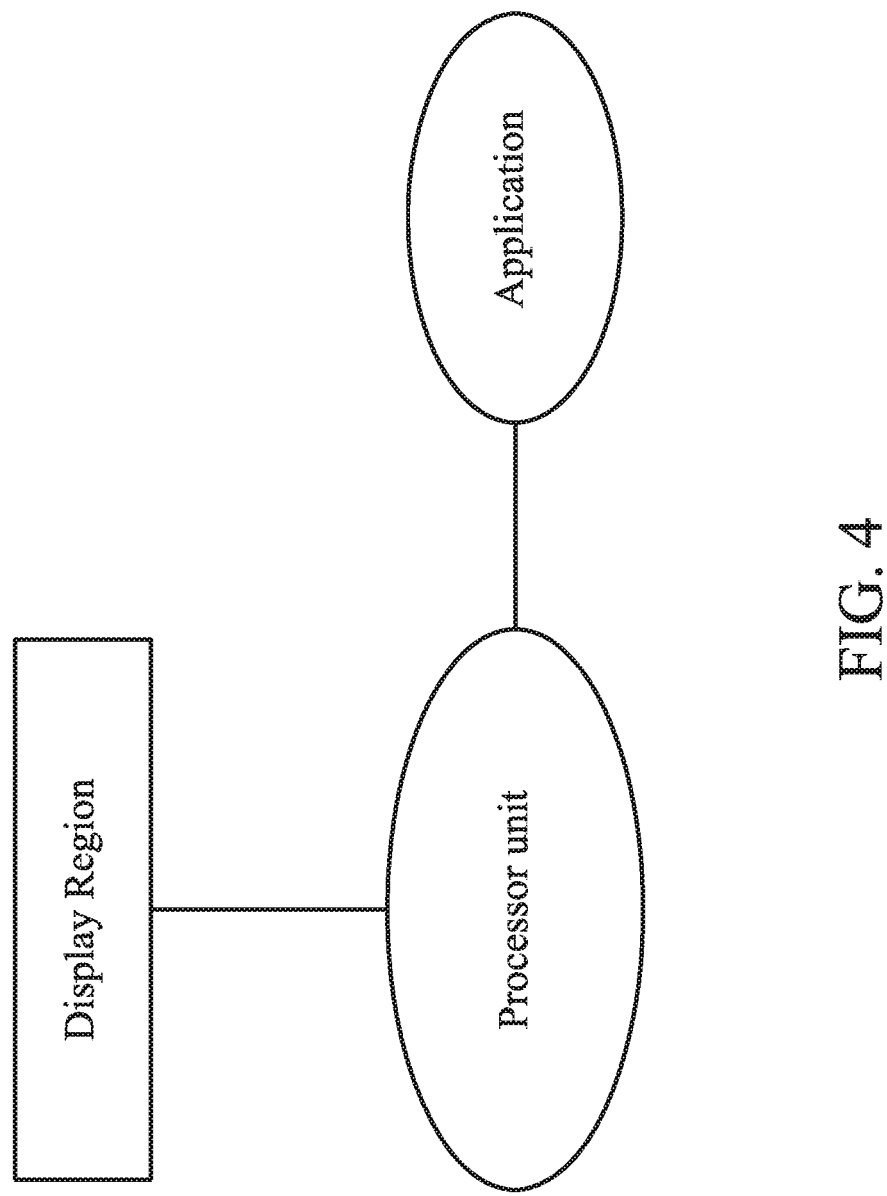
FIG. 4 is a schematic diagram illustrating the electronic device in accordance with some embodiments of the present disclosure.

The protection unit 108A of the present disclosure may be moved manually or automatically. FIG. 3 is a flowchart illustrating an operating method for moving the protection unit 108A according to some embodiments of the present disclosure. FIG. 4 is a schematic diagram illustrating the electronic device 100A in accordance with some embodiments of the present disclosure. Noted that in some embodiments of the present disclosure, the camera module switching from the off-state to the on-state means that the application which may use the camera module is enabled by the user. And after this application is enabled and before it is disabled, the camera module is in the on-state. In addition, in some embodiments of the present disclosure, the camera module switching from the on-state to the off-state means that the application which may use the camera module is disabled by the user. And after this application is disabled and before it is enabled again, the camera module is in the off-state.

Figure 5:
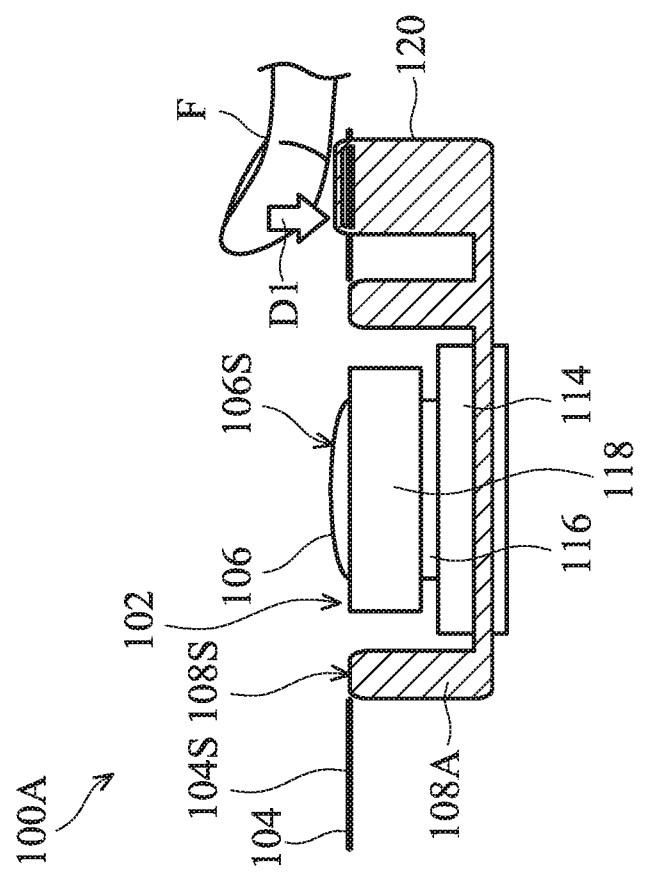
FIG. 5 is a cross-sectional view of an electronic device in accordance with some embodiments of the present disclosure.

The flow at left side in FIG. 3 and the schematic diagram in FIG. 4 depict some embodiments of the present disclosure wherein the protection unit 108A is moved manually. In the step 300S of FIG. 3, the application, such as a camera application, is enabled. Then in step 302S of FIG. 3, a first signal is generated by the application and is transmitted to the processor unit to have the display region 110 display a message to inform the user to move the protection unit 108A manually as shown in FIGS. 4 and 2B. In some other embodiments of the present disclosure, when the electronic device does not include the display region, the electronic device may inform the user by a flashlight or any other suitable lighting element, or by producing a sound or vibration. Then in step 304S of FIG. 3, the protection unit 108A is linearly moved downward along the direction D1 shown in FIG. 2B by the user to make the top surface 108S of the protection unit 108A lower than the surface 106S of the lens 106. In some embodiments of the present disclosure, as shown in FIG. 2B, the direction D1 is substantially perpendicular to the surface 104S of the housing 104. Subsequently, in step 306S, the camera module 102 is ready to capture photos. In some embodiments of the present disclosure, as show FIG. 5, the user may press a bottom 120 which connects to the protection unit 108A by a finger F to move the protection unit 108A relative to the lens 106.

Subsequently, in step 308S, when the user operates to disable the application, a second signal is generated by the application and is transmitted to the processor unit to have the display region 110 display a message to inform the user to move the protection unit 108A manually as shown in FIGS. 4 and 2A. In some other embodiments of the present disclosure, when the electronic device does not include the display region, the electronic device may inform the user by a flashlight or any other suitable lighting element, or by producing a sound or vibration. Then in step 310S of FIG. 3, the protection unit 108A is linearly moved upward along the direction D2 shown in FIG. 2A by the user to make the top surface 108S of the protection unit 108A higher than the surface 106S of the lens 106. In some embodiments of the present disclosure, as shown in FIG. 2A, the direction D2 is substantially perpendicular to the surface 104S of the housing 104. In addition, in some embodiments of the present disclosure, the direction D2 is opposite to the direction D1. Subsequently, in step 312S, the application is disabled and the camera module is in the off-state.

Figure 6:
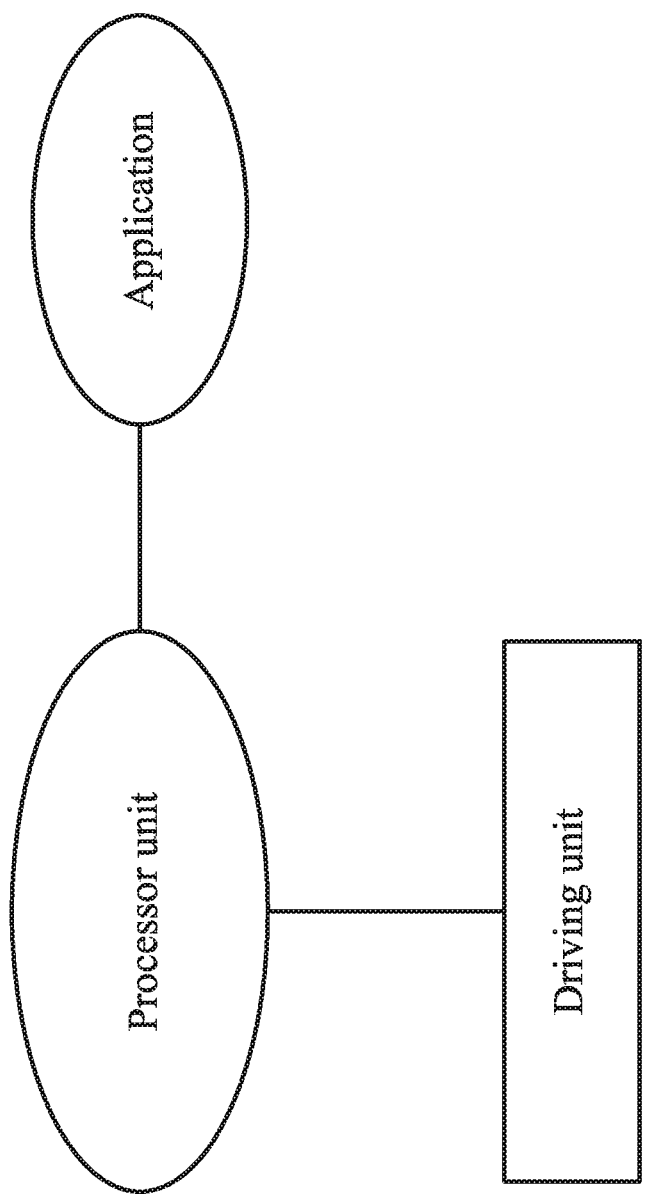
FIG. 6 is a schematic diagram illustrating the electronic device in accordance with some embodiments of the present disclosure.

In some other embodiments of the present disclosure, the protection unit 108A may be moved automatically. The flow at right side in FIG. 3 and the schematic diagram in FIG. 6 depict some embodiments of the present disclosure wherein the protection unit 108A is moved automatically. In the step 300S of FIG. 3, the application, such as a camera application, is enabled. Then in step 314S of FIG. 3, a third signal is generated by the application and is transmitted to the processor unit to have a driving unit move the protection unit 108A as shown in FIGS. 6 and 2B. Then, the protection unit 108A is linearly moved downward along the direction D1 shown in FIG. 2B by the driving unit to make the top surface 108S of the protection unit 108A lower than the surface 106S of the lens 106. In some embodiments of the present disclosure, the driving unit may include a motor or a micro-motor, or magnetic circuit (if protection unit is metal). In some embodiments of the present disclosure, the driving unit may be a voice coil motor or a step motor. In some embodiments of the present disclosure, as shown in FIG. 2B, the direction D1 is substantially perpendicular to the surface 104S of the housing 104. Subsequently, in step 316S, the camera module 102 is ready to capture photos.

Subsequently, in step 318S, when the user operates to disable the application, a fourth signal is generated by the application and is transmitted to the processor unit to have the driving unit move the protection unit 108A as shown in FIGS. 6 and 2A. Then, the protection unit 108A is linearly moved upward along the direction D2 shown in FIG. 2A by the driving unit to make the top surface 108S of the protection unit 108A higher than the surface 106S of the lens 106. In some embodiments of the present disclosure, as shown in FIG. 2A, the direction D2 is substantially perpendicular to the surface 104S of the housing 104. In addition, in some embodiments of the present disclosure, the direction D2 is opposite to the direction D1. Subsequently, in step 312S, the application is disabled and the camera module is in the off-state.

It should be noted that the exemplary embodiment set forth in FIG. 1 is merely for the purpose of illustration. Although the protection unit in FIG. 1 has a square shape or a rectangular shape when viewed from the top view, the protection unit may have other shape. This will be described in detail in the following description. Therefore, the inventive concept and scope are not limited to the exemplary embodiment shown in FIG. 1.

FIGS. 7A-7C is a schematic diagram illustrating the protection unit and the lens in accordance some other embodiments of the present disclosure. As shown in FIGS. 7A-7C, the protection unit 108B has a circular shape and is disposed surrounding the lens 106. The protection unit 108C has an arc shape and is disposed beside the lens 106. The protection unit 108D has a strip shape and is disposed beside the lens 106. Note that FIGS. 7A-7C only shows the protection unit and the lens in order to clearly describe the present disclosure.

It should be noted that the exemplary embodiment set forth in FIGS. 1-2B is merely for the purpose of illustration. In addition to the embodiment set forth in FIGS. 1-2B, the protection unit may have other configuration as shown in FIGS. 8A-9B. This will be described in detail in the following description. Therefore, the inventive concept and scope are not limited to the exemplary embodiment shown in FIGS. 1-2B.

Figure 8A:
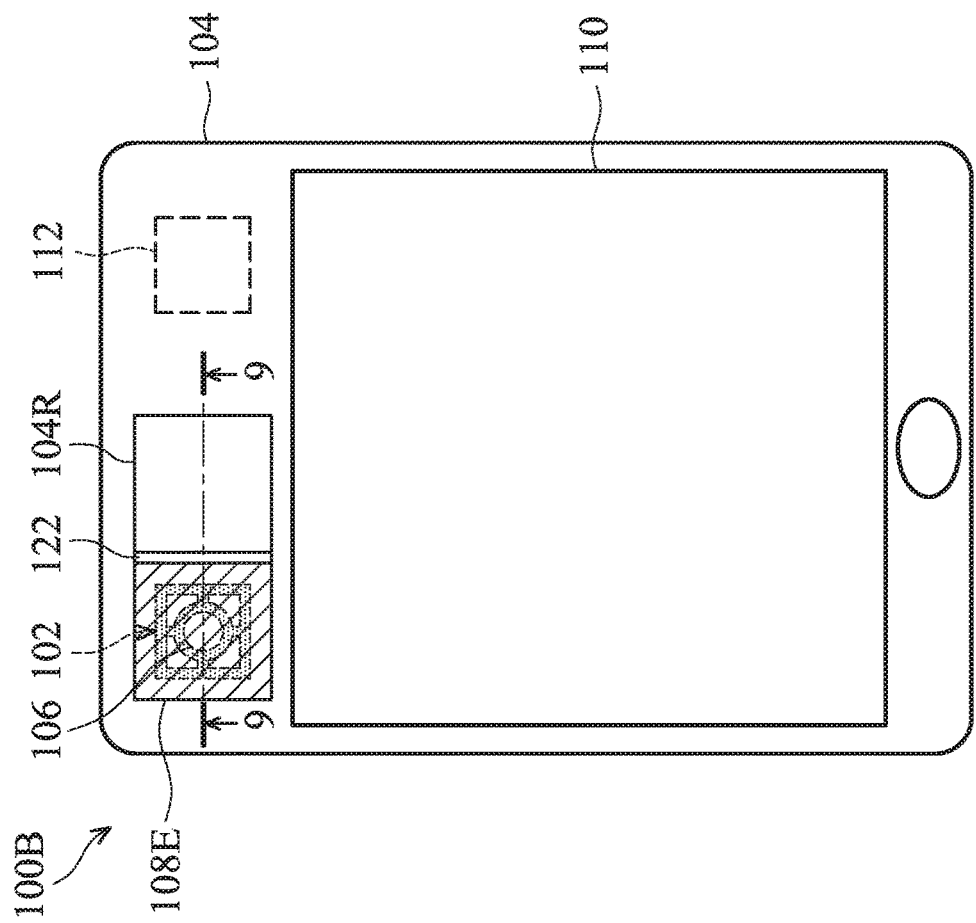
FIG. 8A is a top view of an electronic device when the camera module is in an off-state in accordance with some other embodiments of the present disclosure.
Figure 8B:
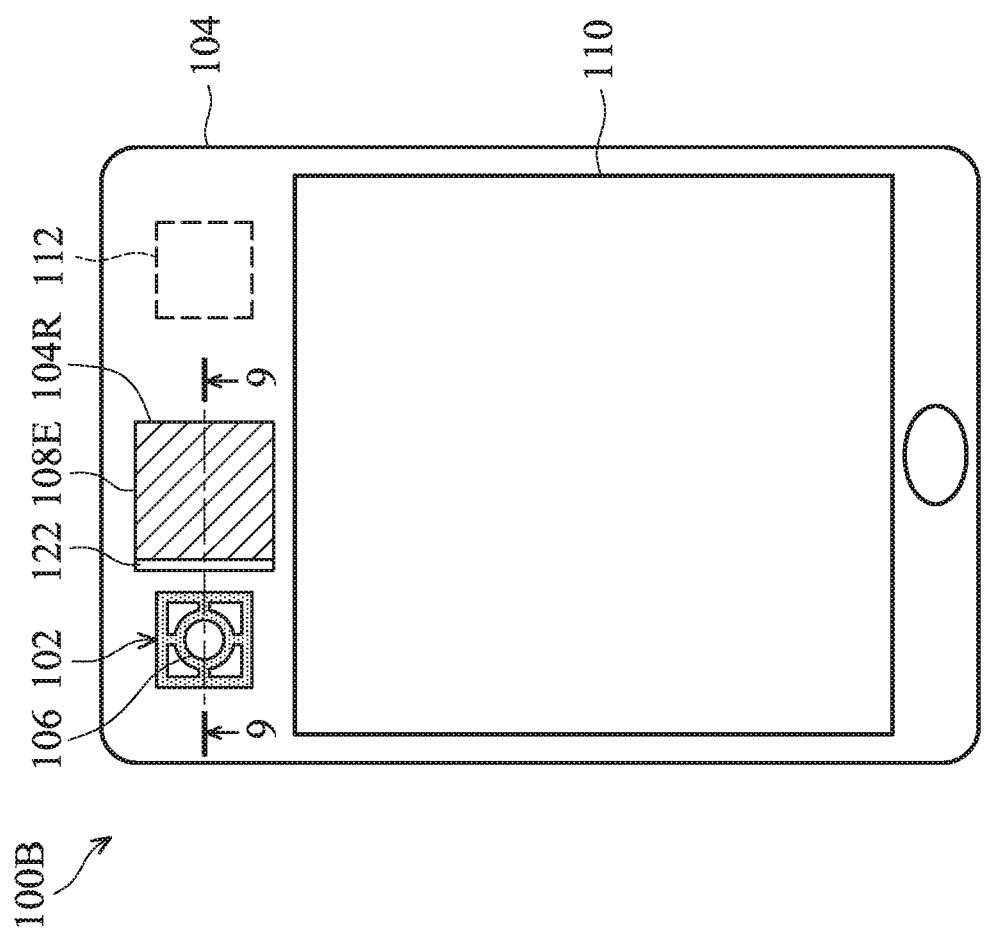
FIG. 8B is a top view of an electronic device when the camera module is in an on-state in accordance with some other embodiments of the present disclosure.
Figure 9B:
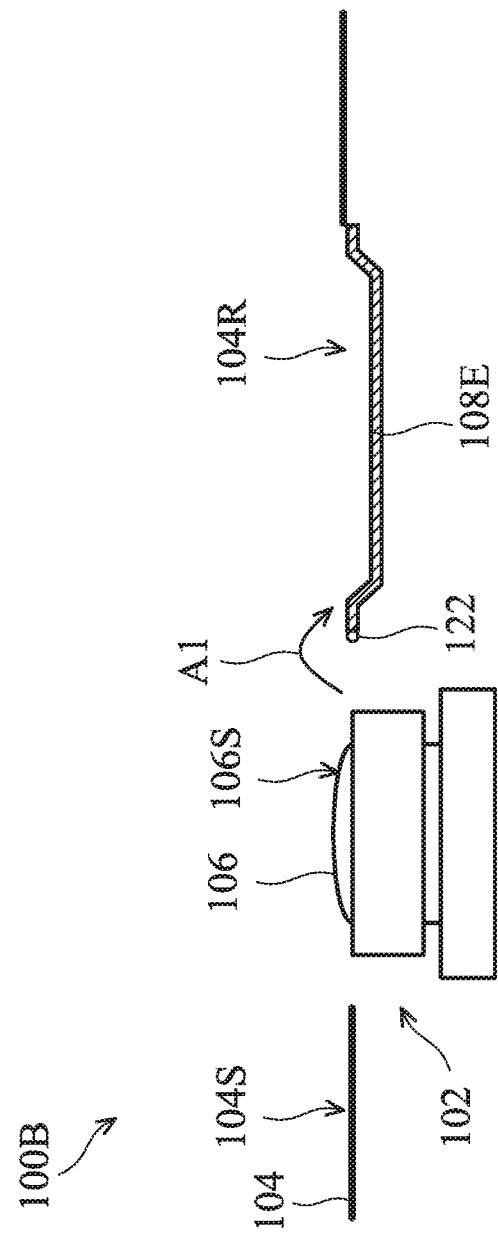
FIG. 9B is a cross-sectional view along line 9-9 in FIG. 8B when the camera module is in an on-state in accordance with some embodiments of the present disclosure.

FIG. 8A is a top view of an electronic device 100B when the camera module is in an off-state in accordance with some other embodiments of the present disclosure. FIG. 8B is a top view of an electronic device 100B when the camera module is in an on-state in accordance with some other embodiments of the present disclosure. FIG. 9A is a cross-sectional view along line 9-9 in FIG. 8A when the camera module is in an off-state in accordance with some embodiments of the present disclosure. FIG. 9B is a cross-sectional view along line 9-9 in FIG. 8B when the camera module is in an on-state in accordance with some embodiments of the present disclosure. Note that the same or similar elements or layers corresponding to those of the electronic device are denoted by like reference numerals. The same or similar elements or layers denoted by like reference numerals have the same meaning and will not be repeated for the sake of brevity.

The difference between the embodiments shown in FIGS. 1-2B and 8A-9B is that the protection unit 108E is a cover plate which has a space to accommodate the lens 106 when the camera module 102 is in the off-state. When the camera module 102 is in the off-state, the protection unit 108E covers the lens 106, and when the camera module 102 is in the on-state, the protection unit 108E exposes the lens 106.

Since the protection unit 108E covers the lens 106 when the camera module 102 is in the off-state, it may prevent the lens from being worn down by other object such as a table. In addition, since the protection unit 108E exposes the lens 106 when the camera module 102 is in the on-state and is ready to capture photos, the field of view of the lens 106 would not be lost. In other words, the camera module 102 may still be able to capture photos with up to 180° field of view or more. Therefore, by utilizing the movable protection unit 108E which is movable relative to the lens 106 of the camera module 102, the electronic device 100B may prevent the lens 106 from being worn down by other object such as a table without losing the field of view of the lens 106.

In particular, as shown in FIGS. 9A-9B, the protection unit 108E is connected to the housing 104 by a joint 122. When the camera module 102 switches from the off-state to the on-state, the protection unit 108E rotates to expose the lens 106 with the joint 122 serving as an axis of rotation as shown by the arrow A1 in FIG. 9B. And when the camera module 102 switches from the on-state to the off-state, the protection unit 108E rotates to cover the lens 106 with the joint 122 serving as the axis of rotation as shown by the arrow A2 in FIG. 9A.

In some embodiments of the present disclosure, the protection unit 108E may be moved manually by the operating method similar to or the same as the flow shown at left side of FIG. 3. Alternatively, in some other embodiments of the present disclosure, the protection unit 108E may be moved automatically by the operating method similar to or the same as the flow shown at right side of FIG. 3. This will not be repeated for the sake of brevity.

In addition, in some embodiments of the present disclosure, the axis of rotation of the joint 122 may be parallel to the surface 104S of the housing 104. In addition, in some embodiments of the present disclosure, the housing 104 has a recess 104R. The recess 104R has a shape similar to or the same as the shape of the protection unit 108E, and when the camera module 102 is in the on-state, the protection unit 108E exposes the lens 106 and is disposed in the recess 104R. However, the disclosure should not be limited thereto. In some other embodiments of the present disclosure, the housing 104 does not have a recess which is used to accommodate the protection unit.

In some embodiments of the present disclosure, the material of the lens 106 in FIGS. 8-9B may include glass, plastic, or any other suitable material. In addition, the glass lens is preferred over the plastic lens since glass is harder than plastic and therefore the glass lens is less likely to be worn down compared to the plastic lens. In addition, in some embodiments of the present disclosure, the lens 106 in FIGS. 8-9B may be a fisheye lens.

It should be noted that the exemplary embodiment set forth in FIGS. 8A-9B is merely for the purpose of illustration. In addition to the embodiment set forth in FIGS. 8A-9B, the protection unit may have other configuration as shown in FIGS. 10A-11B. This will be described in detail in the following description. Therefore, the inventive concept and scope are not limited to the exemplary embodiment shown in FIGS. 8A-9B.

Figure 10A:
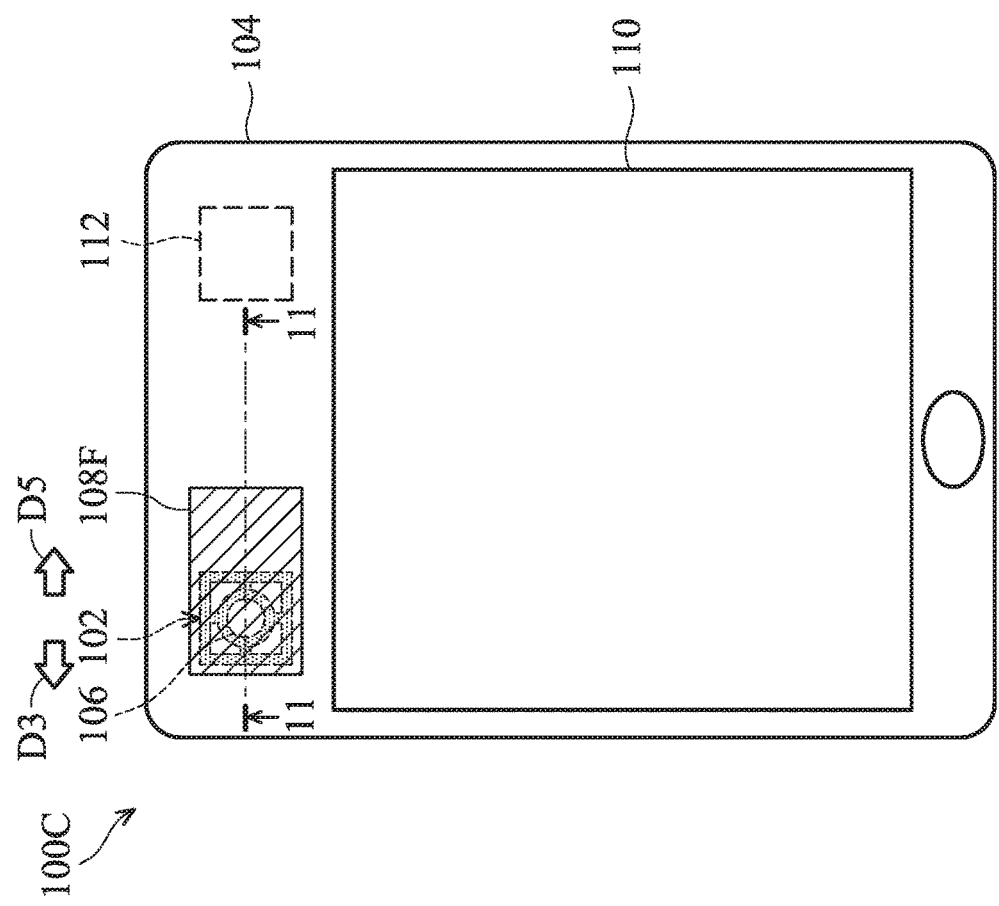
FIG. 10A is atop view of an electronic device when the camera module is in an off-state in accordance with some other embodiments of the present disclosure.
Figure 10B:
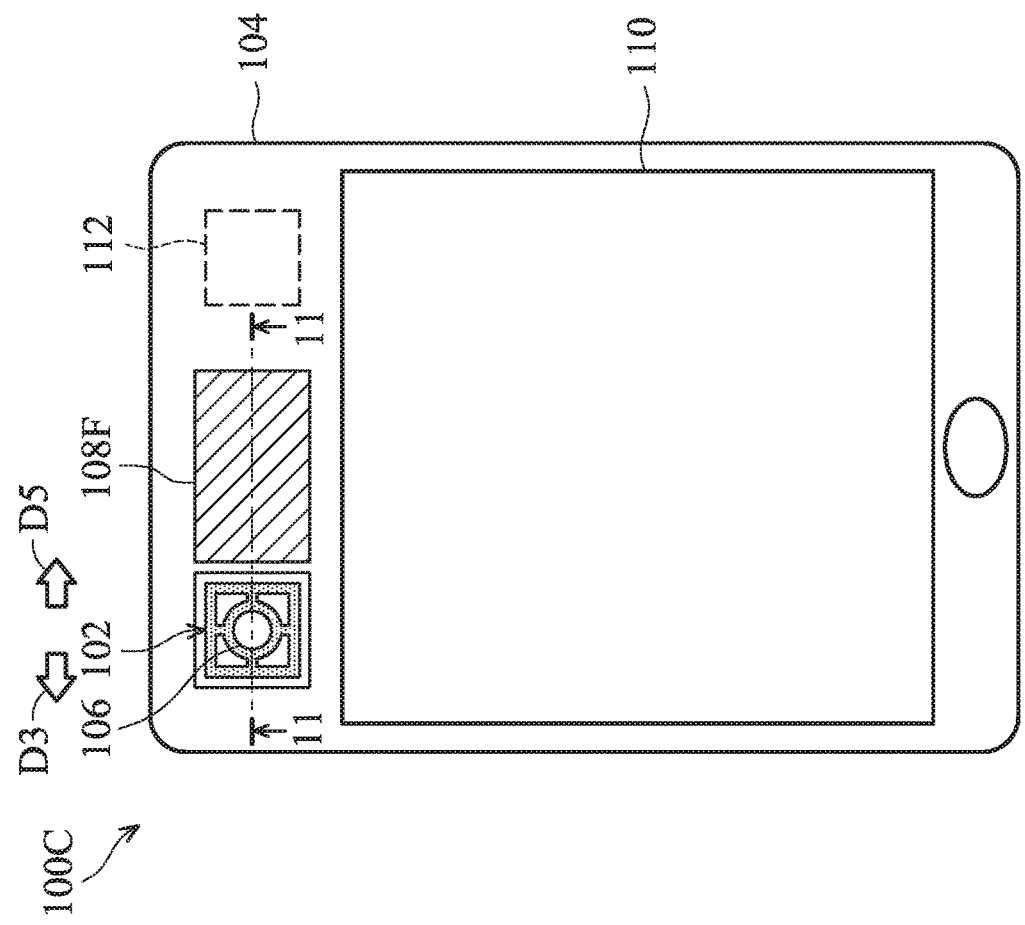
FIG. 10B is a top view of an electronic device when the camera module is in an on-state in accordance with some other embodiments of the present disclosure.
Figure 11B:
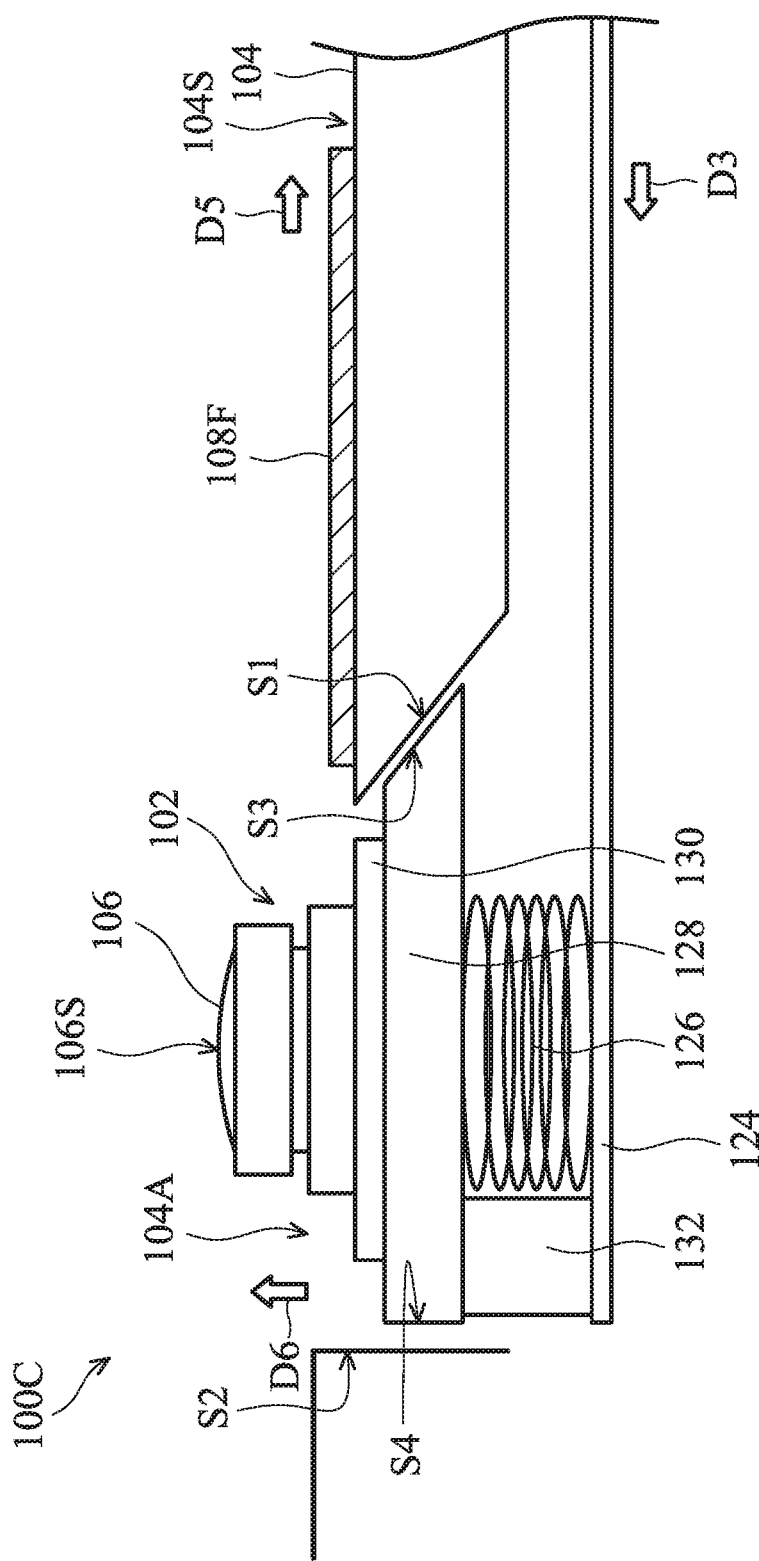
FIG. 11B is a cross-sectional view along line 11-11 in FIG. 10B when the camera module is in an on-state in accordance with some embodiments of the present disclosure.

FIG. 10A is a top view of an electronic device 100C when the camera module 102 is in an off-state in accordance with some other embodiments of the present disclosure. FIG. 10B is a top view of an electronic device 100C when the camera module 102 is in an on-state in accordance with some other embodiments of the present disclosure. FIG. 11A is a cross-sectional along line 11-11 in FIG. 10A when the camera module 102 is in an off-state in accordance with some embodiments of the present disclosure. FIG. 11B is a cross-sectional view along line 11-11 in FIG. 10B when the camera module 102 is in an on-state in accordance with some embodiments of the present disclosure. Note that the same or similar elements or layers corresponding to those of the electronic device are denoted by like reference numerals. The same or similar elements or layers denoted by like reference numerals have the same meaning and will not be repeated for the sake of brevity.

The difference between the embodiments shown in FIGS. 8A-9B and 10A-11B is that the protection unit 108F is a flat cover plate. When the camera module 102 switches from the on-state to the off-state, as shown in FIG. 11A, the protection unit 108F moves along the direction D3 parallel to the surface 104S of the housing 104 to cover the lens 106, and the camera module 102 moves downward along the direction D4 perpendicular to the surface 104S of the housing 104 to make a surface 106S of the lens 106 lower than the surface 104S of the housing 104. When the camera module 102 switches from the off-state to the on-state, as shown in FIG. 11B, the protection unit 108F moves along the direction. D5 parallel to the surface 104S of the housing 104 to expose the lens 106, and the camera module 102 moves upward along the direction D6 perpendicular to the surface 104S of the housing 104 to make the surface 106S of the lens 106 higher than the surface 104S of the housing 104. In some embodiments of the present disclosure, as shown in FIGS. 10A-11B, the direction D3 is opposite to the direction D5, and the direction D4 is opposite to the direction D6.

Since the protection unit 108F covers the lens 106 when the camera module 102 is in the off-state, it may prevent the lens from being worn down by other object such as a table. In addition, since the protection unit 108F exposes the lens 106 when the camera module 102 is in the on-state and is ready to capture photos, the field of view of the lens 106 would not be lost. In other words, the camera module 102 may still be able to capture photos with up to 180° field of view or more. Therefore, by utilizing the movable protection unit 108F which is movable relative to the lens 106 of the camera module 102, the electronic device 100C may prevent the lens 106 from being worn down by other object such as a table without losing the field of view of the lens 106.

In particular, as shown in FIGS. 11A-11B, the housing 104 has an accommodation space 104A, and the camera module 102 is disposed in the accommodation space 104A. In addition, the electronic device 100C may further include a first substrate 124 disposed inside the housing 104, an elastic unit 126 disposed over the first substrate 124, a second substrate 128 disposed over the elastic unit 126, and a circuit board 130 disposed over the second substrate 128. The camera module 102 is disposed over the circuit board 130. In other words, the camera module 102 is disposed over and is connected to the first substrate 124 or the second substrate 128.

In some embodiments of the present disclosure, the elastic unit 126 may include a spring. In some embodiments of the present disclosure, the circuit board 130 may include a rigid printed circuit board or a flexible printed circuit board. In addition, in some embodiments of the present disclosure, the electronic device 100C may further include a wire line 132 connecting the first substrate 124 and the second substrate 128. In some embodiments of the present disclosure, the wire line 132 may include a cable line.

In addition, as shown in FIG. 11B, the accommodation space 104A has a first side S1 and a second side S2 which are opposite to each other, and the second substrate 128 has a third side S3 and a fourth side S4 which are opposite to each other. The first side S1 of the accommodation space 104A and the third side S3 of the second substrate 128 face each other. In addition, the first side S1 of the accommodation space 104A and the third side S3 of the second substrate 128 are both slanted sides and are complementary to each other. In addition, the second side S2 of the accommodation space 104A and the fourth side S4 of the second substrate 128 face each other.

Referring to FIG. 11A, in some embodiments of the present disclosure, when the camera module 102 switches from the on-state to the off-state, the protection unit 108F moves along the direction D3 and toward the second side S2 to cover the lens 106, and the first substrate 124 moves along the direction D5 and toward the first side S1. Since the camera module 102 is connected to the first substrate 124, the camera module 102 is also moved along the direction D5 toward the first side S1. In addition, due to the slanted third side S3 of the second substrate 128 and the slanted first side S1 of the accommodation space 104A, when the camera module 102 is moved toward the first side S1, the camera module 102 would be also moved downward and toward the first substrate 124 to make the surface 106S of the lens 106 lower than the surface 104S of the housing 104.

In addition, as shown in FIG. 11B, when the camera module 102 switches from the off-state to the on-state, the protection unit 108F moves along the direction D5 and toward the first side S1 to expose the lens 106, and the first substrate 124 moves along the direction D3 and toward the second side S2. Since the camera module 102 is connected to the first substrate 124, the camera module 102 is also moved along the direction D3 and toward the second side S2. In addition, since the elastic unit 126 may provide a upward force to the second substrate 128 and the camera module 102, when the camera module 102 is moved toward the second side S2, the camera module 102 would be also moved upward and away from the first substrate 124 to make the surface 106S of the lens 106 higher than the surface 104S of the housing 104.

Figure 12A:
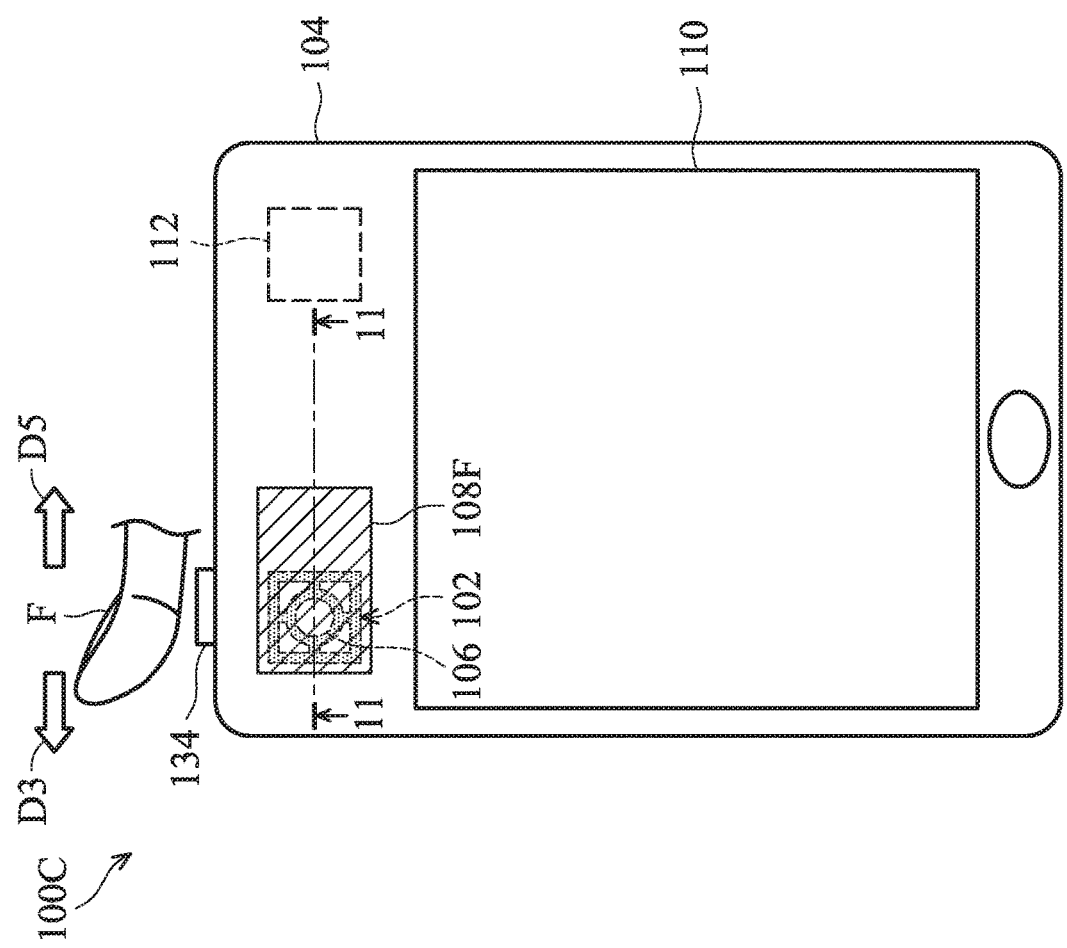
FIG. 12A is a top view of an electronic device when the camera module is in an off-state in accordance with some embodiments of the present disclosure.
Figure 12B:
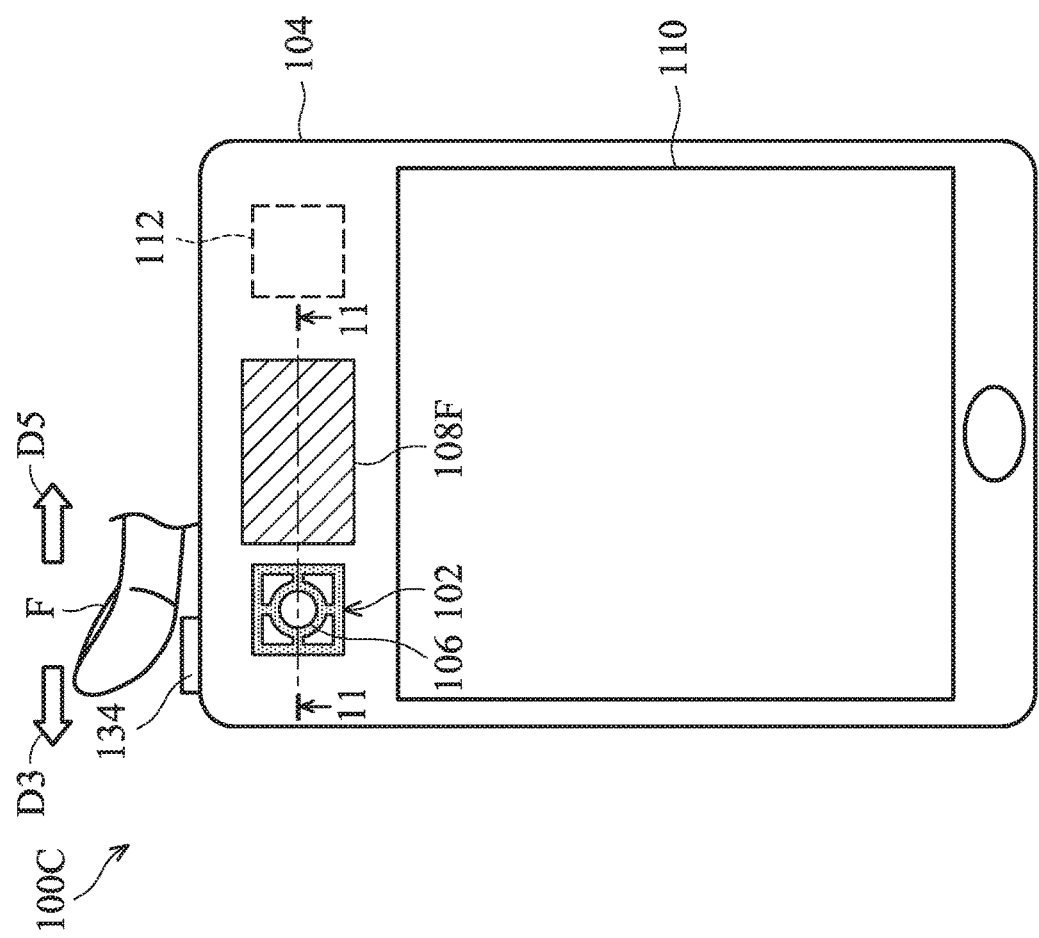
FIG. 12B is a top view of an electronic device when the camera module is in an on-state in accordance with some embodiments of the present disclosure.

In some embodiments of the present disclosure, the protection unit 108F may be moved manually by the operating method similar to or the same as the flow shown at left side of FIG. 3. FIG. 12A is a top view of an electronic device when the camera module is in an off-state in accordance with some embodiments of the present disclosure, and FIG. 12B is a top view of an electronic device when the camera module is in an on-state in accordance with some embodiments of the present disclosure. In some embodiments of the present disclosure, as shown in FIGS. 12A-12B, the electronic device 100C may further include a trigger 134. The trigger 134 operates in conjunction with the first substrate 124 and the protection unit 108F. For example, as shown in FIGS. 12A and 11A, the user may push the trigger 134 by a finger F along the direction D5 to have the first substrate 124 also move along the direction D5 and have the protection unit 108F move along the opposite direction D3 to cover the lens 106. On the other hand, as shown in FIGS. 12B and 11B, the user may push the trigger 134 by a finger F along the direction D3 to have the first substrate 124 also move along the direction D3 and have the protection unit 108F move along the opposite direction D5 to expose the lens 106.

In some other embodiments of the present disclosure, the user may push the trigger 134 by the finger F along the direction D3 to have the first substrate 124 move along the direction D5 and have the protection unit 108F move along the direction D3 to cover the lens 106. In addition, the user may push the trigger 134 by the finger F along the direction D5 to have the first substrate 124 move along the direction D3 and have the protection unit 108F move along the direction D5 to expose the lens 106.

Alternatively, in some other embodiments of the present disclosure, the protection unit 108F may be moved automatically by the operating method similar to or the same as the flow shown at right side of FIG. 3. This will not be repeated for the sake of brevity.

Figure 12C:
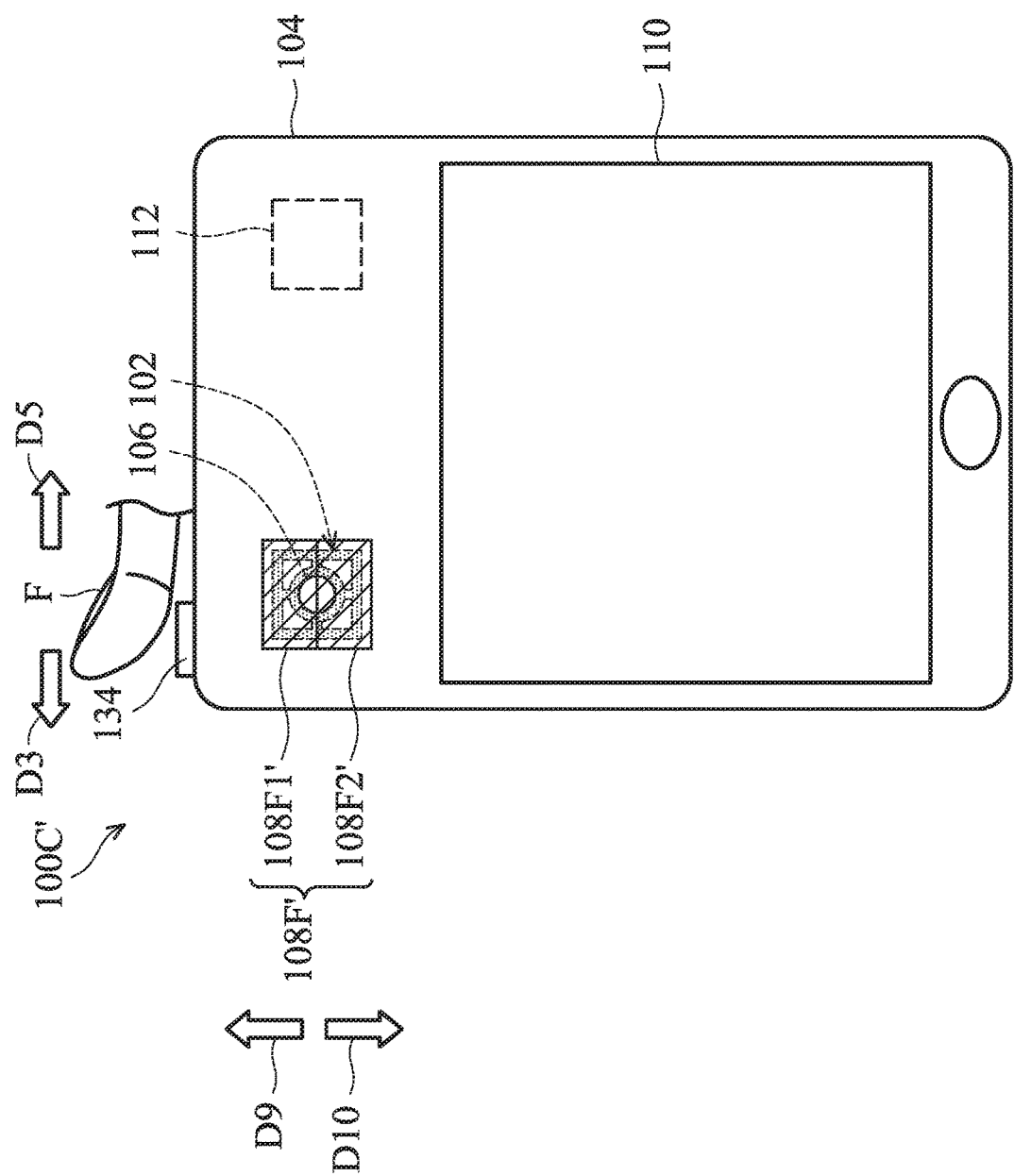
FIG. 12C is a top view of an electronic device when the camera module is in an off-state in accordance with some embodiments of the present disclosure.
Figure 12D:
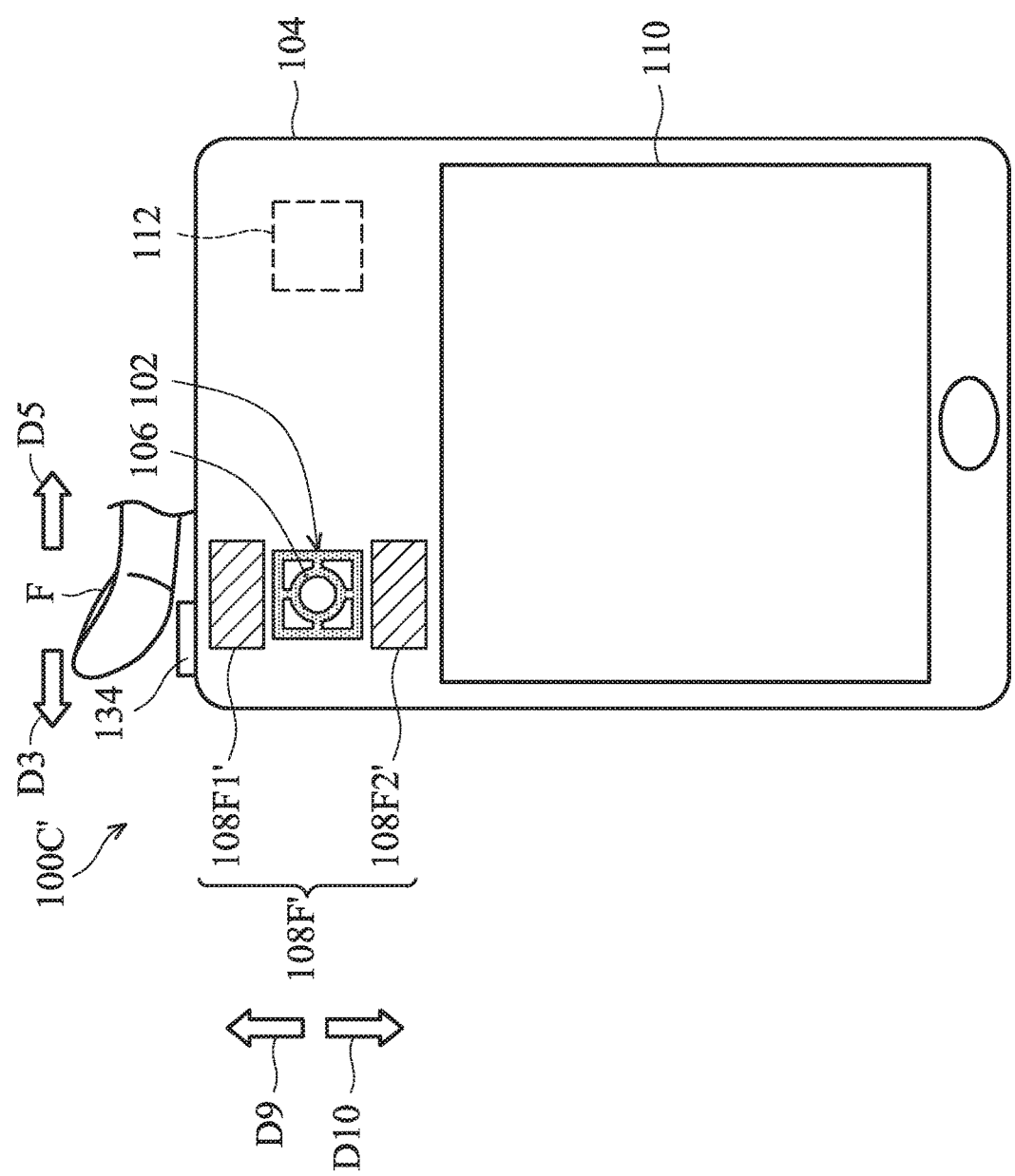
FIG. 12D is a top view of an electronic device when the camera module is in an on-state in accordance with some embodiments of the present disclosure.

In some other embodiments of the present disclosure, the protection unit may have other configurations and may move in other ways. FIG. 12C is a top view of an electronic device 100C' when the camera module 102 is in an off-state in accordance with some other embodiments of the present disclosure. FIG. 12D is a top view of an electronic device 100C' when the camera module 102 is in an on-state in accordance with some other embodiments of the present disclosure. As shown in FIGS. 12C-12D, the protection unit 108F includes a first portion 108F1' and a second portion 108F2'. When the camera module 102 switches from the off-state to the on-state, as shown in FIG. 12D, the first portion 108F1' moves along the direction D9 and the second portion 108F2' moves along the direction D10 which is opposite to the direction D9 to expose the lens 106.

In some embodiments of the present disclosure, the material of the lens 106 in FIGS. 10A-11B may include glass, plastic, or any other suitable material. In addition, the glass lens is preferred over the plastic lens since glass is harder than plastic and therefore the glass lens is less likely to be worn down compared to the plastic lens. In addition, in some embodiments of the present disclosure, the lens 106 in FIGS. 10A-11B may be a fisheye lens.

Figure 14A:
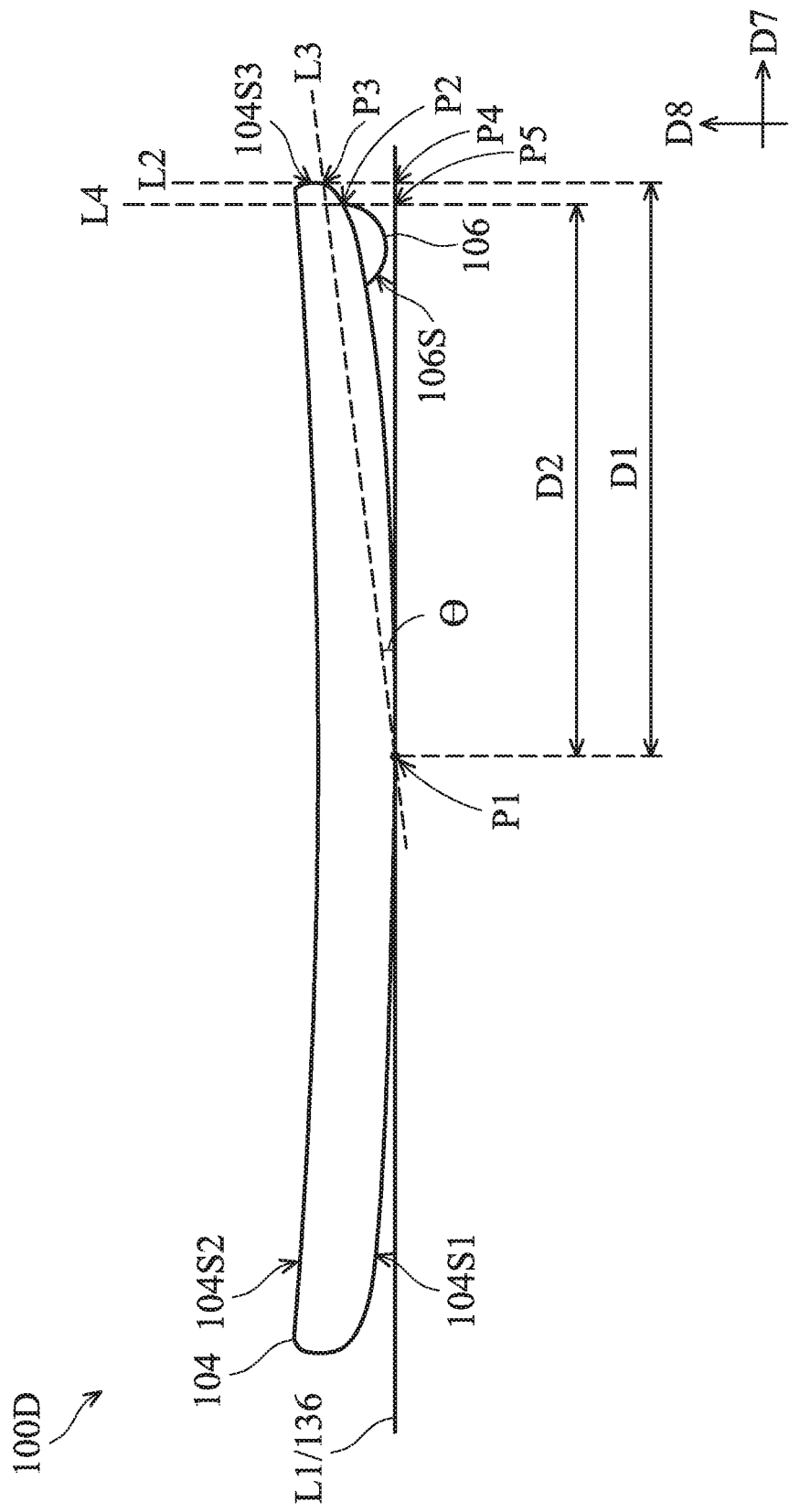
FIG. 14A is a cross-sectional of an electronic device along line 14-14 in FIG. 13 in accordance with some embodiments of the present disclosure.

It should be noted that the exemplary embodiment set forth in FIGS. 1-2B and 8A-11B is merely for the purpose of illustration. In addition to the embodiment set forth in FIGS. 1-2B and 8A-11B, the housing may have other shape as shown in FIGS. 13-14A. This will be described in detail in the following description. Therefore, the inventive concept and scope are not limited to the exemplary embodiment shown in FIGS. 1-2B and 8A-11B.

FIG. 13 is a top view of an electronic device 100D in accordance with some other embodiments of the present disclosure. FIG. 14A is a cross-sectional of the electronic device 100D along line 14-14 in FIG. 13 in accordance with some embodiments of the present disclosure. Note that the same or similar elements or layers corresponding to those of the electronic device are denoted by like reference numerals. The same or similar elements or layers denoted by like reference numerals have the same meaning and will not be repeated for the sake of brevity.

As shown in FIG. 14A, the housing 104 has a first surface 104S1 and a second surface 104S2 opposite to each other. In addition, the housing 104 further includes a third surface 104S3 connecting the first surface 104S1 and the second surface 104S2. In addition, the third surface 104S3 is adjacent to the lens 106. In addition, in some embodiments of the present disclosure, the cross-sectional line 14-14 extends through the center of the lens 106 and is substantially perpendicular to the third surface 104S3 of the housing 104, as shown in FIG. 13.

Still referring to FIGS. 13 and 14A, the camera module 102 is disposed at an end portion of the housing 104, and the lens 106 of the camera module 102 outstands from the housing 104. In addition, the housing 104 has an arc shape, and the second surface 104S2 of the housing 104 is a concave surface of the arc shape as shown in FIG. 14A.

In some embodiments of the present disclosure, as shown in FIG. 14A, the lens 106 outstands from the first surface 104S1 of the housing 104. Since the housing 104 has an arc shape, when the electronic device 100D is put on an object 136 such as a table, the lens 106 would not contact the surface of the object 136. Therefore, this design may prevent the lens from being worn down by the object 136. In addition, since the lens 106 is disposed over the housing 104 which has the arc shape, the field of view of the lens 106 may be equal to or even larger than 180°. In other words, the camera module 102 may be able to capture photos with a field of view equal to or even larger than 180°.

In addition, in some embodiments of the present disclosure, when viewed from a cross-sectional view of FIG. 14A a central point of the first surface 104S1 of the housing 104 is referred to as a first point P1, a point on the surface 106S of the lens 106 which is farthest away from the first point P1 is referred to as a second point P2, a point on the first surface 104S1 which is farthest away from the first point P1 and is adjacent to the second point P2 is referred to as a third point P3, a tangent line which is tangent to the first point P1 is referred to as a first line L1, a line which extends through the first line L1 and the third point P3 and is substantially perpendicular to the first line L1 is referred to as a second line L2, a line which extends through the first point P1 and the third point P3 is referred to as a third line L3, and a line which extends through the first line L1 and the second point P2 and is substantially perpendicular to the first line L1 is referred to as a fourth line L4. In addition, the first line L1 extends along a direction D7, and the second line L2 and fourth line L4 extend along a direction D8 which is substantially perpendicular to the direction D7. In addition, in this embodiment, the first line L1 overlaps with the surface of the object 136.

Still referring to FIG. 14A, the projection distance, which is projected onto the first line L1 along the direction D8, between the first point P1 and the third point P3 is a first distance D1, and the projection distance, which is projected onto the first line L1 along the direction D8, between the first point P1 and the second point P2 is a second distance D2.

In other words, the second line L2 intersects the first line L1 at a point P4, and the fourth line L4 intersects the first line L1 at a point P5. The first distance D1 is the distance between the points P1 and P4, and the second distance D2 is the distance between the points P1 and P5.

In some embodiments of the present disclosure, the first distance D1 ranges from about 40 mm to 150 mm, for example from about 50 mm to 120 mm, or from about 60 mm to 200 mm. In some embodiments of the present disclosure, the second distance D2 ranges from about 20 mm to 135 mm, for example from about 25 mm to 100 mm, or from about 30 mm to 90 mm, or 40 mm to 80 mm, or 45 mm to 70 mm.

In some embodiments of the present disclosure, the ratio of the second distance D2 to the first distance D1 ranges from about 0.5 to 1.0. For example, the ratio may range from about 0.6 to 0.95, from about 0.7 to 0.9, or from about 0.8 to 0.85. Note that if the ratio of the second distance D2 to the first distance D1 does not range from about 0.5 to 1.0, for example less than 0.5, the lens 106 would be likely to contact the object 136 and would be easily worn down by the object 136.

Still referring to FIG. 14A, the third line L3 intersects the first line L1 at an acute angle θ. In some embodiments of the present disclosure, the acute angle θ is greater than about 0.1 degree. For example, the acute angle may be greater than about 0.2 degree or about 1 degree. Note that if the acute angle θ is not greater than about 0.1 degree, the lens 106 would be likely to contact the object 136 and would be easily worn down by the object 136.

It should be understood that the terms "about" and "substantially" typically mean +/−20% of the stated value, more typically +/−10% of the stated value, more typically +/−5% of the started value, more typically +/−3% of the stated value, more typically +/−2% of the stated value, more typically +/−1% of the stated value and even more typically +/−0.5% of the stated value. The stated value of the present disclosure is an approximate value. When there is no specific description, the stated value includes the meaning of "about" or "substantially".

In some embodiments of the present disclosure, the material of the lens 106 may include glass, plastic, or any other suitable material. In addition, the glass lens is preferred over the plastic lens since glass is harder than plastic and therefore the glass lens is less likely to be worn down compared to the plastic lens. In addition, in some embodiments of the present disclosure, the lens 106 in FIGS. 13-14 may be a fisheye lens.

Figure 14B:
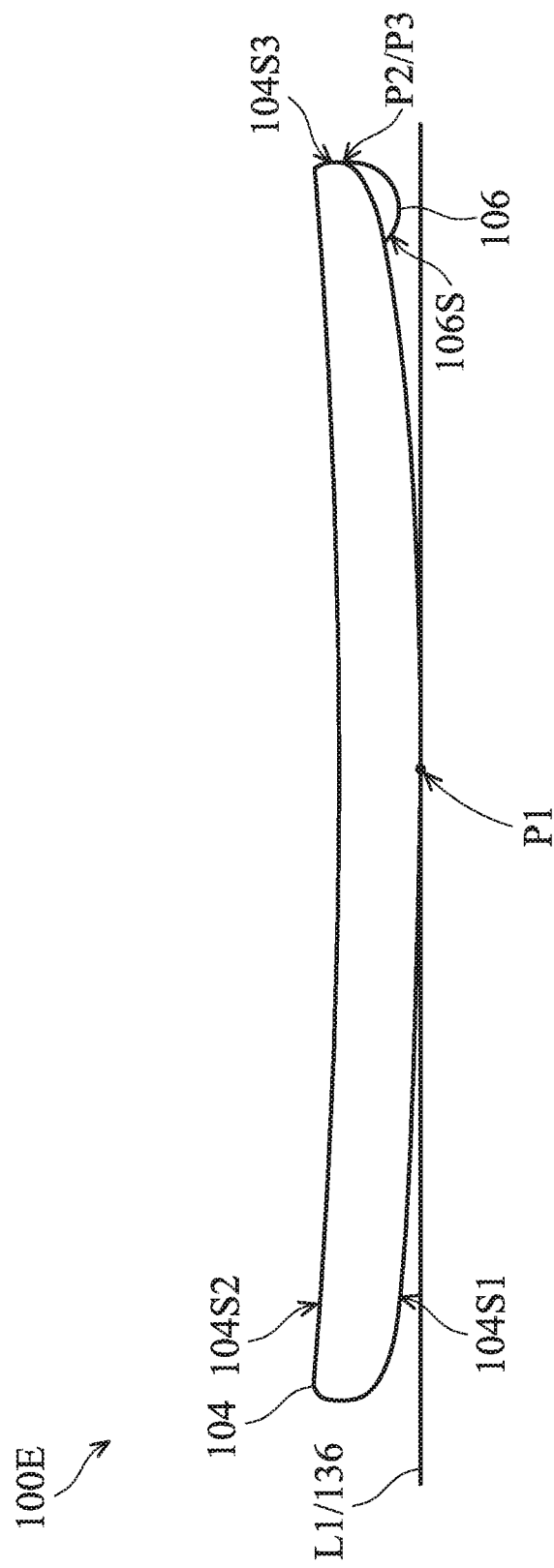
FIG. 14B is a cross-sectional of an electronic device in accordance with some other embodiments of the present disclosure.

FIG. 14B is a cross-sectional of an electronic device 100E in accordance with some embodiments of the present disclosure. In some embodiments of the present disclosure, as shown in FIG. 14B, the ratio of the second distance D2 to the first distance D1 is 1.0. In addition, the second point P2 of the lens 106 directly contacts the third surface 104S3. In addition, the second point P2 may overlap with the third point P3.

Figure 14C:
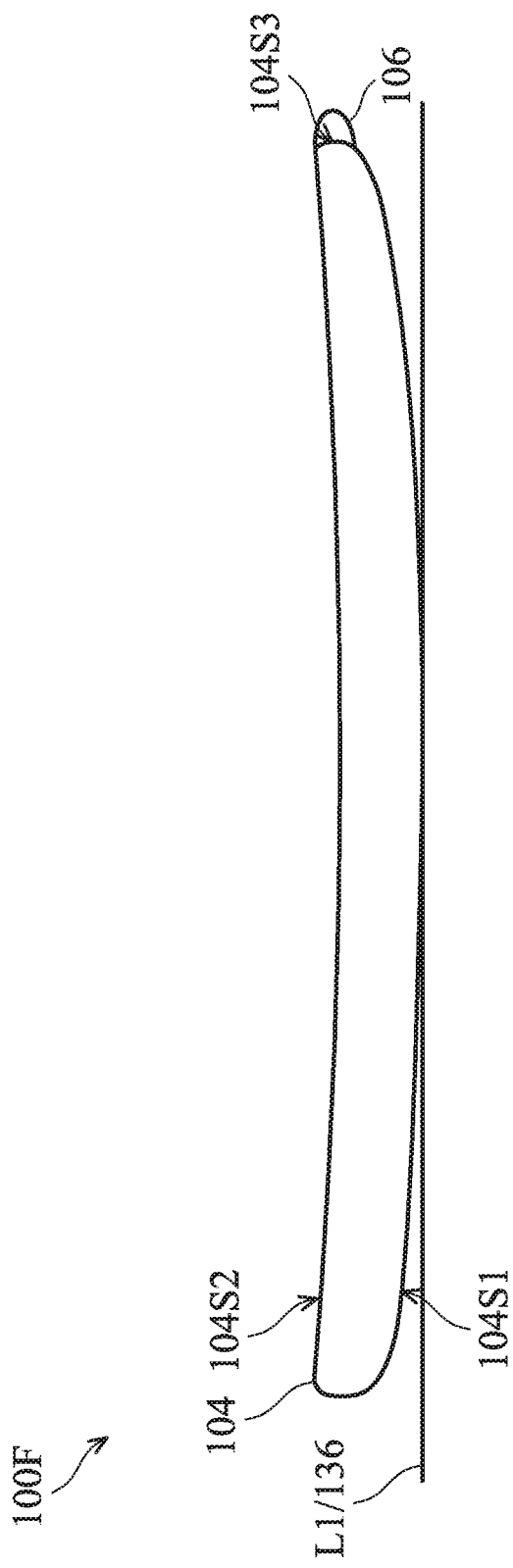
FIG. 14C is a cross-sectional of an electronic device in accordance with some other embodiments of the present disclosure.

FIG. 14C is a cross-sectional of an electronic device 100F in accordance with some other embodiments of the present disclosure. The difference between the embodiments shown in FIGS. 13-14B and 14C is that the lens 106 outstands from the third surface 104S3 of the housing 104. Since the lens 106 outstands from the third surface 104S3 of the housing 104, when the electronic device 100F is put on an object 136 such as a table, the lens 106 would not contact the surface of the object 136. Therefore, this design may prevent the lens from being worn down by the object 136. In addition, the camera module of the electronic device 100F may be able to capture photos with a field of view equal to or even larger than 180°.

In addition, in some embodiments of the present disclosure, the electronic devices 100D-100F shown in FIGS. 13-14C may not include any protection unit aforementioned. However, in some other embodiments of the present disclosure, the electronic devices 100D-100F shown in FIGS. 13-14C may include any one of the aforementioned protection units.

In summary, the embodiment of the present disclosure utilizes a movable protection unit which is movable relative to the lens of the camera module in the electronic device or utilizes a housing which has an arc shape to prevent the lens from being worn down without losing the field of view of the lens.

Note that the above element sizes, element parameters, and element shapes are not limitations of the present disclosure. Those skilled in the art can adjust these settings or values according to different requirements. It is understood that the electronic device of the present disclosure are not limited to the configurations of FIGS. 1 to 14C. The present disclosure may merely include any one or more features of any one or more embodiments of FIGS. 1 to 14C In other words, not all of the features shown in the figures should be implemented in the electronic device and method for manufacturing the same of the present disclosure.

Although some embodiments of the present disclosure and their advantages have been described in detail, it should be understood that various changes, substitutions and alterations can be made herein without departing from the spirit and scope of the disclosure as defined by the appended claims. For example, it will be readily understood by those skilled in the art that many of the features, functions, processes, and materials described herein may be varied while remaining within the scope of the present disclosure. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. An electronic device, comprising:
a housing;
a camera module disposed in the housing and having a lens outstanding from a surface of the housing; and
a protection unit connected to the housing,
wherein when the camera module is in an off-state, a top surface of the protection unit is higher than a surface of the lens,
when the camera module is in an on-state, the top surface of the protection unit is lower than the surface of the lens, and wherein the protection unit moves along a direction perpendicular to the surface of the housing between the on-state and the off-state.

2. The electronic device as claimed in claim 1, wherein the protection unit has a circular shape, an arc shape, a square shape, strip shape, or a rectangular shape.

3. The electronic device as claimed in claim 1, wherein a material of the lens comprises plastic or glass.

4. The electronic device as claimed in claim 1, wherein the lens is a fisheye lens.

5. An electronic device, comprising:
a housing;
a camera module disposed in the housing and having a lens; and
a protection unit connected to the housing,
wherein when the camera module is in an off-state, the protection unit covers the lens,
when the camera module is in an on-state, the lens outstands from a surface of the housing and the protection unit exposes the lens,
wherein the protection unit is connected to the housing by a joint,
when the camera module switches from the off-state to the on-state, the protection unit rotates to expose the lens with the joint serving as an axis of rotation,
when the camera module switches from the on-state to the off-state, the protection unit rotates to cover the lens with the joint serving as the axis of rotation,
wherein the axis of rotation is parallel to the surface of the housing.

6. The electronic device as claimed in claim 5, wherein the housing has a recess, wherein when the camera module is in an on-state, the protection unit exposes the lens and is disposed in the recess.

7. The electronic device as claimed in claim 5, wherein a material of the lens comprises plastic or glass.

8. The electronic device as claimed in claim 5, wherein the lens is a fisheye lens.

9. An electronic device, comprising:
a housing;
a camera module disposed in the housing and having a lens;
a protection unit connected to the housing, wherein when the camera module is in an off-state, the protection unit covers the lens,
when the camera module is in an on-state, the lens outstands from a surface of the housing and the protection unit exposes the lens,
wherein when the camera module switches from the on-state to the off-state, the protection unit moves along a first direction parallel to the surface of the housing to cover the lens, and the camera module moves along a second direction perpendicular to the surface of the housing to make a surface of the lens lower than the surface of the housing,
when the camera module switches from the off-state to the on-state, the protection unit moves along a third direction parallel to the surface of the housing to expose the lens, and the camera module moves along a fourth direction perpendicular to the surface of the housing to make the surface of the lens higher than the surface of the housing, wherein the first direction is opposite to the third direction, and the second direction is opposite to the fourth direction,
wherein the housing has an accommodation space having a first side and a second side which are opposite to each other,
wherein the camera module is disposed in the accommodation space and is disposed over a first substrate,
when the camera module switches from the on-state to the off-state, the protection unit moves toward the second side to cover the lens, and the first substrate moves toward the first side and the camera module moves toward the first side and toward the first substrate to make the surface of the lens lower than the surface of the housing,
when the camera module switches from the off-state to the on-state, the protection unit moves toward the first side to expose the lens, and the first substrate moves toward the second side and the camera module moves toward the second side and moves away from the first substrate to make the surface of the lens higher than the surface of the housing;
an elastic unit disposed over the first substrate; and
a second substrate disposed over the elastic unit and having a third side and a fourth side which are opposite to each other, wherein the first side of the accommodation space and the third side of the second substrate face each other and are both slanted sides, wherein the camera module is disposed over the second substrate.

* * * * *